US008828669B2

(12) United States Patent
Browning et al.

(10) Patent No.: US 8,828,669 B2
(45) Date of Patent: Sep. 9, 2014

(54) METHODS OF SCREENING FOR A COMPOUND THAT INHIBITS THE INTERACTION BETWEEN BAFF AND BCMA

(75) Inventors: Jeffrey Browning, Brookline, MA (US); Christine Ambrose, Reading, MA (US); Fabienne MacKay, Vaucluse (AU); Jurg Tschopp, Epalinges (CH); Pascal Schneider, Epalinges (CH); Jeffrey Thompson, Stoneham (MA)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 13/401,610

(22) Filed: Feb. 21, 2012

(65) Prior Publication Data

US 2012/0214687 A1    Aug. 23, 2012

Related U.S. Application Data

(63) Continuation of application No. 12/500,909, filed on Jul. 10, 2009, now abandoned, which is a continuation of application No. 10/077,137, filed on Feb. 15, 2002, now Pat. No. 7,691,804, which is a continuation of application No. PCT/US00/22507, filed on Aug. 16, 2000.

(60) Provisional application No. 60/183,536, filed on Feb. 18, 2000, provisional application No. 60/181,684, filed on Feb. 11, 2000, provisional application No. 60/149,378, filed on Aug. 17, 1999.

(51) Int. Cl.
*G01N 33/53* (2006.01)
*A61K 39/395* (2006.01)
*A61K 38/17* (2006.01)
*C07K 14/705* (2006.01)
*A61K 39/00* (2006.01)

(52) U.S. Cl.
CPC ......... *A61K 39/395* (2013.01); *A61K 2039/505* (2013.01); *A61K 38/17* (2013.01); *C07K 14/70575* (2013.01); *C07K 2319/00* (2013.01); *A61K 39/00* (2013.01)
USPC ........................................................ 435/7.1

(58) Field of Classification Search
None
See application file for complete search history.

(56) References Cited

U.S. PATENT DOCUMENTS

| 5,969,102 | A  | 10/1999 | Bram et al. |
| 6,297,367 | B1 | 10/2001 | Tribouley |
| 6,316,222 | B1 | 11/2001 | Bram et al. |
| 6,475,986 | B1 | 11/2002 | Aggarwal |
| 6,475,987 | B1 | 11/2002 | Shu |
| 6,541,224 | B2 | 4/2003  | Yu et al. |
| 6,774,106 | B2 | 8/2004  | Theill et al. |
| 2002/0037852 | A1 | 3/2002  | Browning et al. |
| 2002/0086018 | A1 | 7/2002  | Theill et al. |
| 2002/0165156 | A1 | 11/2002 | Browning et al. |
| 2003/0023038 | A1 | 1/2003  | Rennert et al. |
| 2003/0082175 | A1 | 5/2003  | Schneider et al. |
| 2004/0013674 | A1 | 1/2004  | Ambrose et al. |
| 2004/0072188 | A1 | 4/2004  | Ambrose et al. |
| 2006/0067933 | A1 | 3/2006  | Gross et al. |

FOREIGN PATENT DOCUMENTS

| EP | 0 869 180 A1 | 10/1998 |
| WO | WO 97/33902 | 9/1997 |
| WO | WO 98/18921 | 5/1998 |
| WO | WO 98/27114 | 6/1998 |
| WO | WO 98/55620 | 12/1998 |
| WO | WO 98/55621 | 12/1998 |
| WO | WO 99/11791 | 3/1999 |
| WO | WO 99/12964 | 3/1999 |
| WO | WO 99/12965 | 3/1999 |
| WO | WO 99/13078 | 3/1999 |
| WO | WO 99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/50633 | 8/2000 |
| WO | WO 00/68378 | 11/2000 |
| WO | WO 01/24811 | 4/2001 |
| WO | WO 01/87977 | 11/2001 |
| WO | WO 01/87979 | 11/2001 |
| WO | WO 02/02641 | 1/2002 |
| WO | WO 02/18620 | 3/2002 |
| WO | WO 03/055979 | 7/2003 |

OTHER PUBLICATIONS

Agrawal, et al., "Antisense therapeutics: is it as simple as complementary base recognition?" *Molecular Med. Today*., Q:72-81 (2000).
Avery et al., *The Journal of Clinical Investigation*, 112(2):286-297 (2003).
Bork et al., "Go hunting in sequence databases but watch out for the traps" *TIG* 12(10):425-427 (1996).
Bork, "Powers and Pitfalls in Sequence Analysis: The 70% Hurdle" *Genome Research*, 10:398-400 (2000).
Branch, "A good antisense molecule is hard to find" *Trends in Biochem. Sci.* 23: 45-50 (1998).
Brenner, "Errors in Genome Annotation" *TIG* 15(4):132-133 (1999).
Burgess et al., "Possible Dissociation of Heparin-binding and Mitogenic Activities of the Heparin-binding (Acidic Fibroblast) Growth Factor-1 from its Receptor-binding Activities by Site-directed Mutagenesis of a Single Lysine Residue" *The Journal of Cell Biology*, 111:2129-2138 (1990).
Chirila, et al., "The use of synthetic polymers for delivery of therapeutic antisense oligodeoxynucleotides" *Biomaterials*, 23: 321-342 (2002).
Chiu et al., *Blood*, 109(2):729-732 (2007).

(Continued)

*Primary Examiner* — Patricia A Duffy
(74) *Attorney, Agent, or Firm* — Finnegan, Henderson, Farabow, Garrett & Dunner, LLP.

(57) ABSTRACT

A novel receptor in the TNF family is provided: BAFF-R. Chimeric molecules and antibodies to BAFF-R and methods of use thereof are also provided.

2 Claims, 19 Drawing Sheets

(56) References Cited

OTHER PUBLICATIONS

Crooke, *Antisense Res. and Application*, Chapter 1, pp. 1-50 (1998).
Doerks et al. "Protein Annotation: detective work for function predication" *TIG*, 14(6):248-230(1998).
Goding, *Immunology and Cell Biology*, 81:497-498 (2003).
Gras et al., "BCMAp: An integral membrane protein in the Golgi apparatus of human mature B lymphocytes," *Int. Immunology* 7(7):1093-1106 (1995).
Gross et al., "TACI and BCMA are receptors for a TNF homologue implicated in B-Cell autoimmune disease," *Nature*, 404:995-999 (2000).
Hahne et al., "APRIL, a new ligand of the tumor necrosis family, stimulates tumor cell growth," *J. Exp. Med* 188(6):1185-1190 (1998).
Hu, *DNA and Cell Biology*, 12(8):763-770 (1993).
Kashii, Y. et al., "Constitutive expression and role of the family ligands in apoptotic killing of tumor cells by human NK cells," *J. Immunol.* 163:5358-66 (1999).
Kwon et al., "Single amino acid substitutions of $\alpha_1$—Antitrypsin that confer enhancement in thermal stability," *J. Biol. Chem.*, 269:9627-9631 (1994).
Laabi et al., "The BCMA gene, Preferentially expressed during B lymphoid maturation, 13 bidirectionally transcribed," *Nucleic Acids Res.* 22(7):1147-1154 (1994).
Laabi et al., "A new gene, BCM, on Chromosome 16 is Fused to the Interleukin 2 Gene by a t(4;16)(q26,p13) Translocation in a Malignant T Cell Lymphoma," *The EMBO J.* 11:3897-3904 (1992).
Lazar et al., "Transforming Growth Factor a: Mutation of Aspartic Acid 47 and Leucine 48 Results in Different Biological Activities" *Molecular and Cellular Biology*, 8(3):1247-1252 (1988).
Mackay, et al., "BAFF: A Fundamental Survival Factor for B Cells" *Nature Reviews Immunology*, 2:465-475 (2002).
Madry et al., "The Characterization of Murine BCMA Gene Defines it as a New Member of the Tumor Necrosis Factor Receptor Superfamily" *Internation Immunonology*, 10(11):1696-1702 (1998).
Maini and Zyberk, *Scand. J. Rheumatol. Suppl.*, 76:237-242 (1988) (abstract).
Mayer et al., *Clinical Immunology and Immunopathology 61*(2 p. 2)S28-S36 (1991).
Miller et al., "Genetic Studies of the lac Repressor," *J.Mol. Biol.* 131:191-222 (1979).
Moreland et al., "Etanercept Therapy in Rheumatoid Arthritis, a Randomized, Controlled Trial," *Ann. Intern. Med.* 130:478-486 (1999).
Novak et al., *Blood*, 103(2):689-694 (2004).
Ngo et al., "Computational Complexity, Protein Structure Prediction, and the Levinthal Paradox," *The Protein Folding Problem and Tertiary Structure Prediction*, Birkhauser, Boston 1994 490-495 (1994).
O'Connor et al., *Journal of Experimental Medicine*, 199(1):91-97 (2004).
Peracchi, "Prospects for antiviral ribozymes and deoxyribozymes," *Rev. Med. Virol.*, 142:47-64 (2004).
Pitti et al., "Genomic Amplification of a Decoy Receptor for Fas Ligand in Lung and Colon Cancer" *Nature*, 396:669-703 (1998).
Rudinger et al., "Characteristics of Amino acids as components of a peptide hormone sequence" in *Peptide Hormones*, Edited by Parson, J.A., University Park Press, p. 6 (1976).
Schiemann et al, "A Essential Role for BAFF in the Normal Development of B Cells Through a BCMA—Independent Pathway," *Science*, 293:2111-2114 (2001).
Schneider et al., "BAFF, A Novel Ligand of the Tumor Necrosis Factor Family, Stimulates B Cell Growth," *J. Exp. Med.*, 189:(11) 1747-1756 (1999).
Schiemann et al., *Science*, 293:2111-2114 (2001).
Skolnick et al., "From genes to protein structure and function: novel application of computation approaches in genomic era" *Trends in Biotech*, 18(1):34-39 (2000).
Smith et al., "The TNF Receptor Superfamily of Cellular and Viral Proteins: Activation, Costimulation, and Death," *Cell* 76:959-962 (1994).
Smith et al., The Challenges of genome sequence annotation or "the devil is in the details" *Nature Biotechnology*, 15:1222-1223 (1997).
Thompson et al., "BAFF Binds to the Tumor Necrosis Factor Receptor-like Molecule B Cell Maturation Antigen and is important for Maintaining the Peripheral B Cell Population," *J. Exp. Med*, 192:129-135 (2000).
Thompson et al., "BAFF Inteacts with Orphan Receptor, BCMA" *Scandinavian Journal of Immunology*, 51 (suppl 1):65 (2000).
Ward, P. and Mulligan, M. "Blocking of adhesion molecules in vivo as anti-inflammatory therapy," *Ther. Immunol.* 1:165-71 (1994).
Ware, C., "APRIL and BAFF Connect Autoimmunity and Cancer," *J. Exp. Med.* 192:F35-37 (2000).
Waldschmidt et al., *Science*, 293:2012-2013 (2001).
Von Bulow & Bram, "NF-AT Activation Induced by a Caml-Interacting Member of the Tumor Necrosis Factor Receptor Superfamily," *Science* 278:138-141 (1997).
Xia et al., "TACI is a TRAF-interacting Receptor for TALL-1, a Tumor Necrosis Factor Family Member Involved in B Cell Regulation," *J. Exp. Med.* 192:137-143 (2000).
Yu et al., "APRIL and TALL-1 and receptors BCMA and TACI: System for regulating humoral immunity," *Nature Immunology*, 1:252-256 (2000).

```
  1 ATG GAG ACA GAC ACA CTC CTG CTA TGG GTG CTG CTC CTC TGG GTT CCA GGT TCC ACT GGT
SEQ ID 4    1▸ M   E   T   D   T   L   L   L   W   V   L   L   L   W   V   P   G   S   T   G
SEQ ID 3 61 GAC GTC ACG ATG TTG CAG ATG CTT CAA CTT GAC TTT GAC AGT TTG
            1▸
 21▸         D   V   T   M   L   Q   M   L   Q   L   D   F   D   S   L
121 TTG CAT GCT TGC ATA CCT CAA CTT CGA TGC CAA CCT CTA ACA TGT
 18▸ L   H   A   C   I   P   Q   L   R   C   Q   P   L   T   C
 41▸ L   H   A   C   I   P   Q   L   R   C   Q   P   L   T   C
181 CAG CGT TAT AAT GCA AGT GTG TCA AAA GGA AAA ACT CAC ACA
 38▸ Q   R   Y   N   A   S   V   S   K   G   K   T   H   T
 61▸ Q   R   Y   N   A   S   V   S   K   G   K   T   H   T
241 TGC CCA CCA TGC CCA GCA CCT GAA CTC CTC GGG GGA CCG TCA GTC TTC CTC TTC CCC CCA
 81▸ C   P   P   C   P   A   P   E   L   L   G   G   P   S   V   F   L   F   P   P
301 AAA CCC AAG GAC ACC CTC ATG ATC TCC CGG ACC CCT GAG GTC ACA TGC GTG GTG GTG GAC
101▸ K   P   K   D   T   L   M   I   S   R   T   P   E   V   T   C   V   V   V   D
361 GTG AGC CAC GAA GAC CCT GAG GTC AAG TTC AAC TGG TAC GTG GAC GGC GTG GAG GTG CAT
121▸ V   S   H   E   D   P   E   V   K   F   N   W   Y   V   D   G   V   E   V   H
421 AAT GCC AAG ACA AAG CCG CGG GAG GAG CAG TAC AAC AGC ACG TAC CGT GTG GTC AGC GTC
141▸ N   A   K   T   K   P   R   E   E   Q   Y   N   S   T   Y   R   V   V   S   V
481 CTC ACC GTC CTG CAC CAG GAC TGG CTG AAT GGC AAG GAG TAC AAG TGC AAG GTC TCC AAC
```

FIG. 2A

```
161▸     L   T   V   L   H   Q   D   W   L   N   G   K   E   Y   K   C   K   V   S   N
541     AAA ACC GCC CTC CCA GCC CCC ATC GAG AAA ACC ATC TCC AAA GCC AAA GGG CAG CCC CGA GAA

181▸     K   A   L   P   A   P   I   E   K   T   I   S   K   A   K   G   Q   P   R   E
601     CCA CAG GTC TAC ACC CTG CCC CCA TCC CGG GAT GAG CTG ACC AAG AAC CAG GTC AGC CTG

201▸     P   Q   V   Y   T   L   P   P   S   R   D   E   L   T   K   N   Q   V   S   L
661     ACC TGC CTG GTC AAA GGC TTC TAT CCC AGC GAC ATC GCC GTG GAG TGG GAG AGC AAT GGG

221▸     T   C   L   V   K   G   F   Y   P   S   D   I   A   V   E   W   E   S   N   G
721     CAG CCG GAG AAC AAC TAC AAG ACC ACG CCT CCC GTG TTG GAC TCC GAC GGC TCC TTC TTC

241▸     Q   P   E   N   N   Y   K   T   T   P   P   V   L   D   S   D   G   S   F   F
781     CTC TAC AGC AGG CTA ACC GTG GAC AAG AGC AGG TGG CAG CAG GGG AAC GTC TTC TCA TGC

261▸     L   Y   S   K   L   T   V   D   K   S   R   W   Q   Q   G   N   V   F   S   C
841     TCC GTG ATG CAT GAG GCT CTG CAC AAC CAC TAC ACG CAG AAG AGC CTC TCC CTG TCT CCC

281▸     S   V   M   H   E   A   L   H   N   H   Y   T   Q   K   S   L   S   L   S   P
901     GGG AAA TGA

```
                                                              BsaAI          BbsI
  1  AAGACTCAAA  CTTAGAAACT  TGAATTAGAT  GTGGTATTCA  AATCCTTACG  TGCCGCGAAG
 61  ACACAGACAG  CCCCCGTAAG  AACCCACGAA  GCAGGCGAAG  TTCATTGTTC  TCAACATTCT
                                EcoRI
121  AGCTGCTCTT  GCTGCATTTG  CTCTGGAATT  CTTGTAGAGA  TATTACTTGT  CCTTCCAGGC
          SfcI                           BclI
181  TGTTCTTTCT  GTAGCTCCCT  TGTTTTCTTT  TTGTGATCAT  GTTGCAGATG  GCTGGGCAGT
                                            1▶ M    L    Q    M    A    G    Q
                SspI                   SphI               HincII
241  GCTCCCAAAA  TGAATATTTT  GACAGTTTGT  TGCATGCTTG  CATACCTTGT  CAACTTCGAT
   8▶ C   S   Q   N   E   Y   F   D   S   L   H   A   C   I   P   C   Q   L   R
                              PciI
                              AflIII
301  GTTCTTCTAA  TACTCCTCCT  CTAACATGTC  AGCGTTATTG  TAATGCAAGT  GTGACCAATT
  28▶ C   S   S   N   T   P   P   L   T   C   Q   R   Y   C   N   A   S   V   T   N
                                          BsmFI
361  CAGTGAAAGG  AACGAATGCG  ATTCTCTGGA  CCTGTTTGGG  ACTGAGCTTA  ATAATTTCTT
  48▶ S   V   K   G   T   N   A   I   L   W   T   C   L   G   L   S   L   I   I   S
421  TGGCAGTTTT  CGTGCTAATG  TTTTTGCTAA  GGAAGATAAG  CTCTGAACCA  TTAAAGGACG
  68▶ L   A   V   F   V   L   M   F   L   L   R   K   I   S   S   E   P   L   K   D
         DraI            AlwI     BsaI
481  AGTTTAAAAA  CACAGGATCA  GGTCTCCTGG  GCATGGCTAA  CATTGACCTG  GAAAAGAGCA
  88▶ E   F   K   N   T   G   S   G   L   L   G   M   A   N   I   D   L   E   K   S
            XmnI                    StuI     XhoI
541  GGACTGGTGA  TGAAATTATT  CTTCCGAGAG  GCCTCGAGTA  CACGGTGGAA  GAATGCACCT
 108▶ R   T   G   D   E   I   I   L   P   R   G   L   E   Y   T   V   E   E   C   T
                                                SalI
                                                HincII
       BbsI                                     AccI
601  GTGAAGACTG  CATCAAGAGC  AAACCGAAGG  TCGACTCTGA  CCATTGCTTT  CCACTCCCAG
 128▶ C   E   D   C   I   K   S   K   P   K   V   D   S   D   H   C   F   P   L   P
661  CTATGGAGGA  AGGCGCAACC  ATTCTTGTCA  CCACGAAAAC  GAATGACTAT  TGCAAGAGCC
 148▶ A   M   E   E   G   A   T   I   L   V   T   T   K   T   N   D   Y   C   K   S
          PvuII
721  TGCCAGCTGC  TTTGAGTGCT  ACGGAGATAG  AGAAATCAAT  TTCTGCTAGG  TAATTAACCA
 168▶ L   P   A   A   L   S   A   T   E   I   E   K   S   I   S   A   R
         XhoI                   DraI                                       BglII
781  TTTCGACTCG  AGCAGTGCCA  CTTTAAAAAT  CTTTTGTCAG  AATAGATGAT  GTGTCAGATC
841  TCTTTAGGAT  GACTGTATTT  TTCAGTTGCC  GATACAGCTT  TTTGTCCTCT  AACTGTGGAA
                                                                            StyI
901  ACTCTTTATG  TTAGATATAT  TTCTCTAGGT  TACTGTTGGG  AGCTTAATGG  TAGAAACTTC
961  CTTGGTTTCA  TGATTAAAGT  CTTTTTTTTT  CCTGA
```

FIG. 3

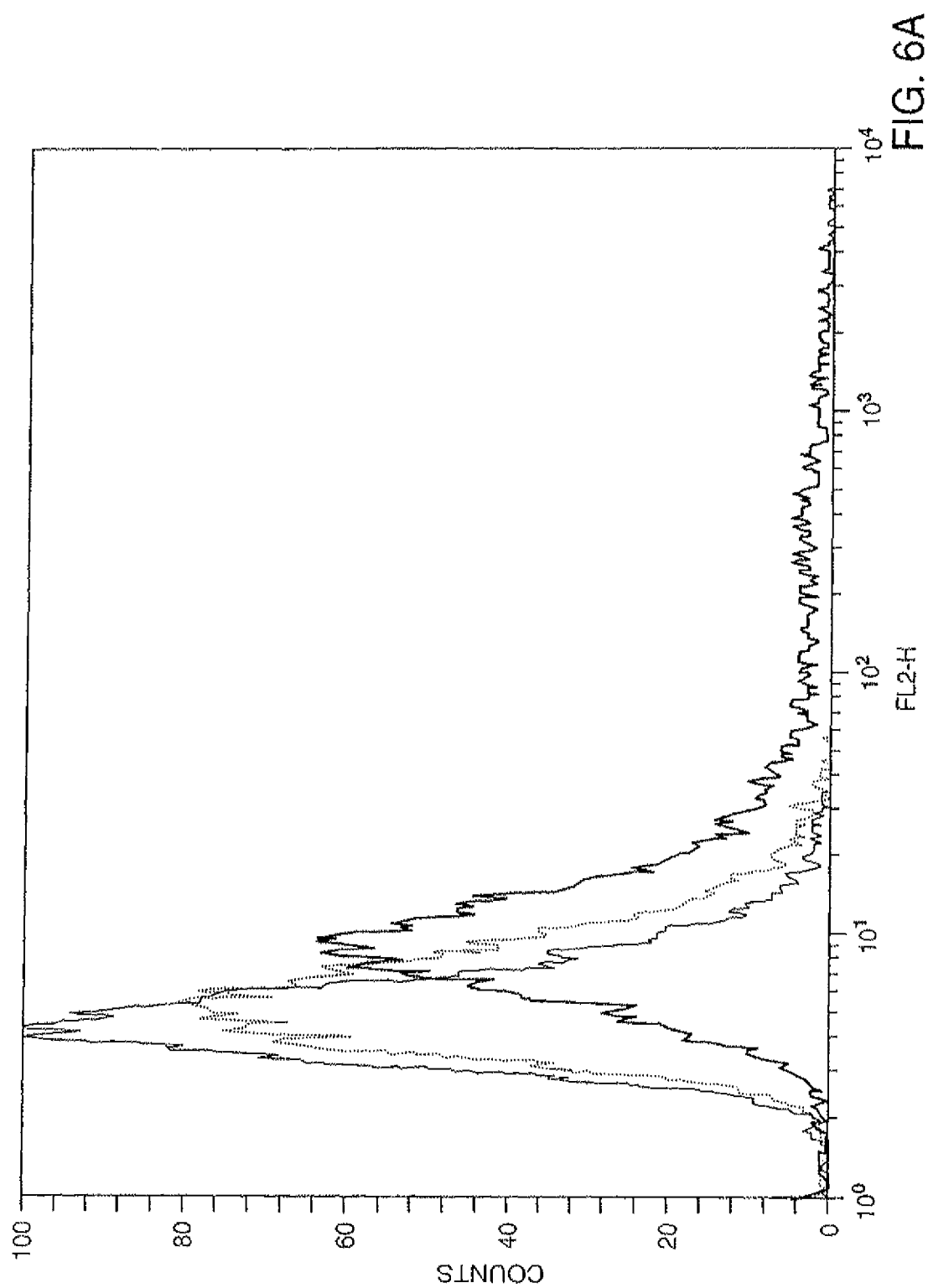

| Marker | Left | Right | Events | % Gated | % Total | Mean | Geo Mean | CV | Median |
|---|---|---|---|---|---|---|---|---|---|
| All | 1. | 9910 | 10000 | 100.00 | 100.00 | 26.59 | 7.74 | 576.94 | 5.94 |
| M1 | 17. | 9910 | 1313 | 13.13 | 13.13 | 161.35 | 60.77 | 246.67 | 42.94 |

| Marker | Left | Right | Events | % Gated | % Total | Mean | Geo Mean | CV | Median |
|---|---|---|---|---|---|---|---|---|---|
| All | 1. | 9910 | 10000 | 100.00 | 100.00 | 12.39 | 6.54 | 405.32 | 5.47 |
| M1 | 17. | 9910 | 876 | 8.76 | 8.76 | 78.94 | 43.41 | 195.84 | 33.68 |

| Marker | Left | Right | Events | % Gated | % Total | Mean | Geo Mean | CV | Median |
|---|---|---|---|---|---|---|---|---|---|
| All | 1. | 9910 | 10000 | 100.00 | 100.00 | 6.99 | 6.60 | 69.06 | 5.67 |
| M1 | 17. | 9910 | 393 | 3.93 | 3.93 | 24.33 | 23.31 | 33.78 | 21.48 |

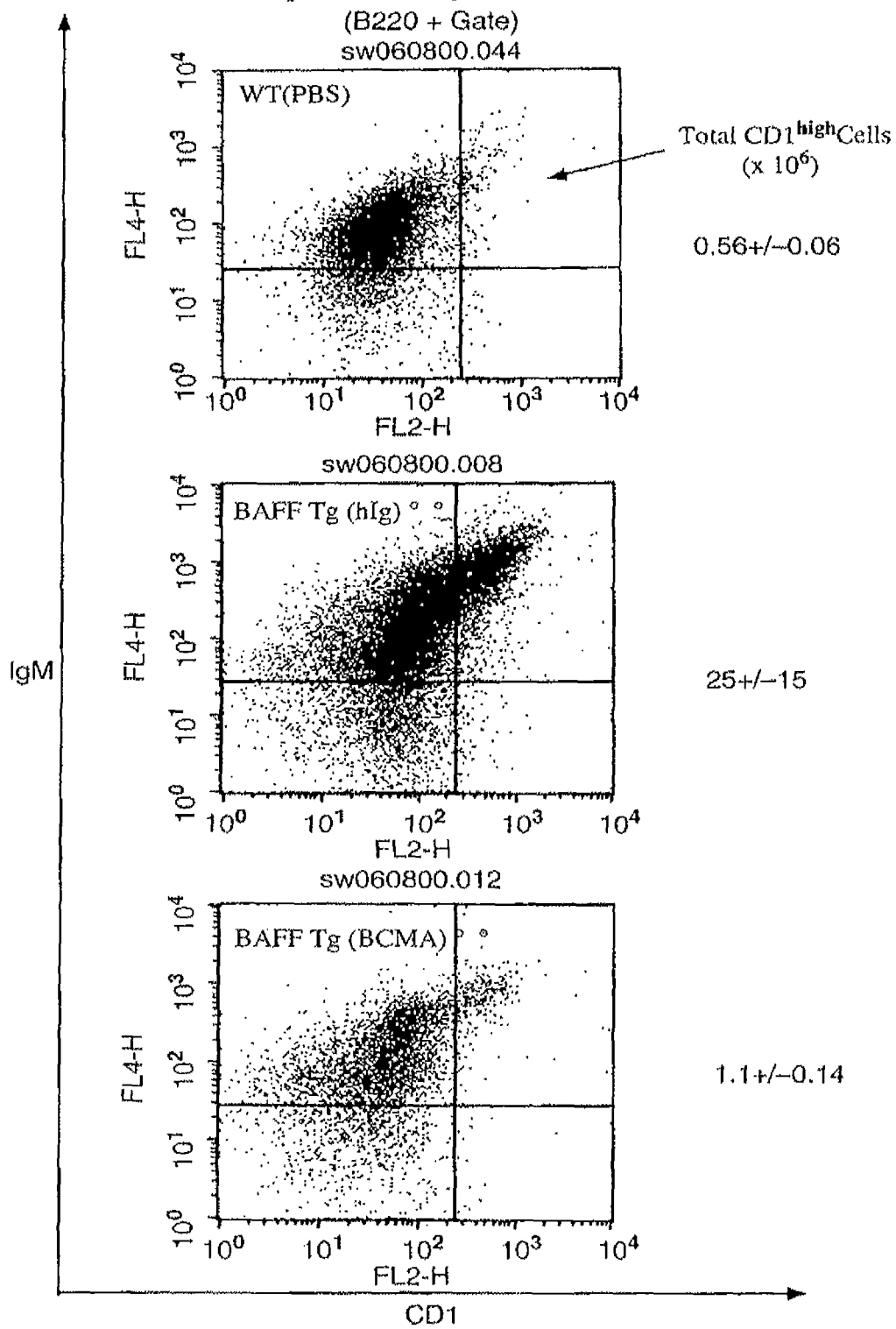
FIG. 10A BCMA-Ig Treatment Reduces Total CD1$^{hi}$/IgM$^{hi}$ B Cell Populations in Spleens of Baff Tg Mice

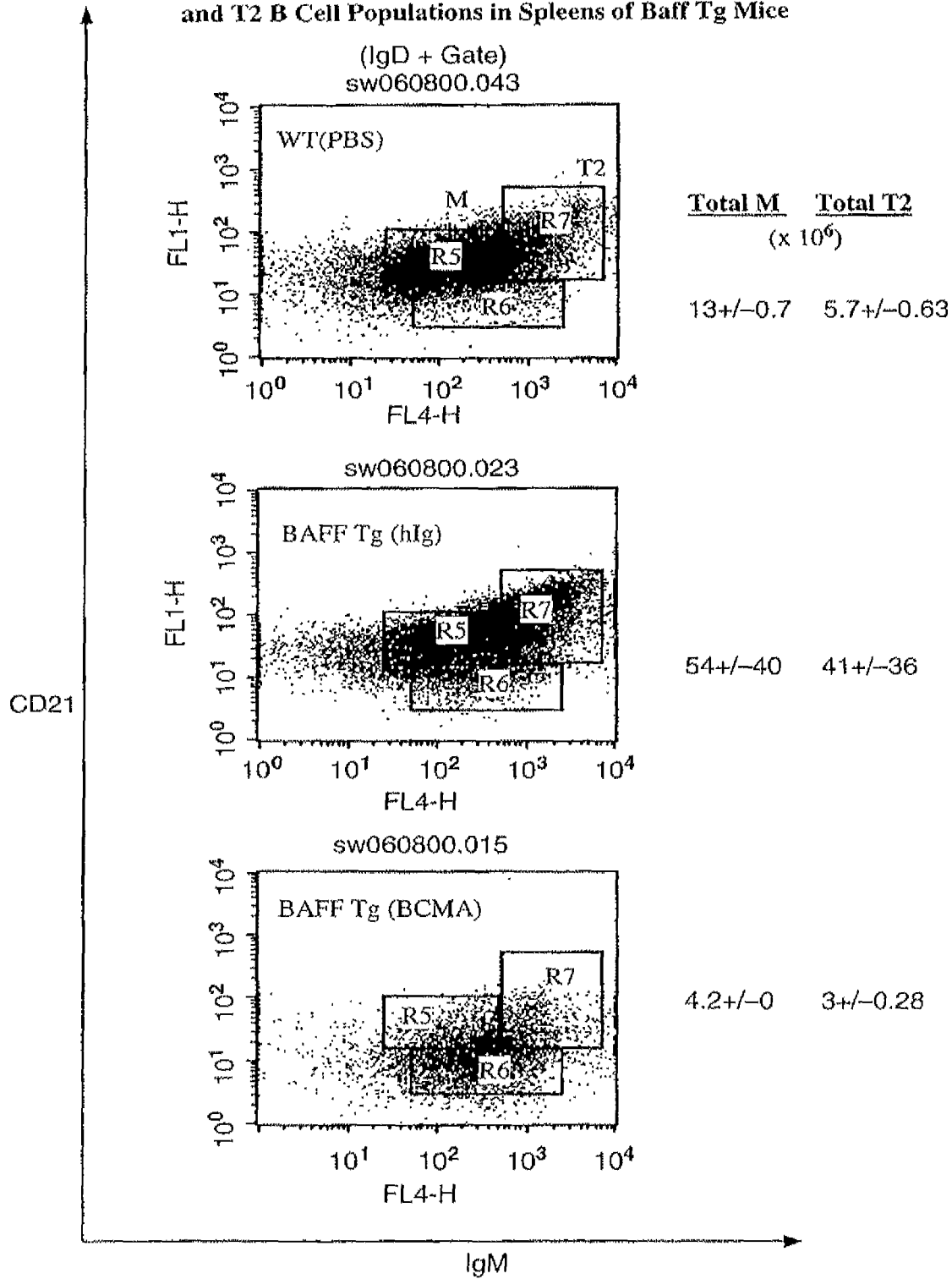
FIG. 10B BCMA-Ig Treatment Reduces Total Mature B and T2 B Cell Populations in Spleens of Baff Tg Mice BCMA-Ig Treatment Reduces Total Marginal Zone and T1 B Cell Populations in Spleens of Baff Tg Mice

US 8,828,669 B2

METHODS OF SCREENING FOR A COMPOUND THAT INHIBITS THE INTERACTION BETWEEN BAFF AND BCMA

RELATED APPLICATIONS

This is a continuation of application Ser. No. 12/500,909, filed Jul. 10, 2009 (abandoned), which is a continuation of U.S. patent application Ser. No. 10/077,137, filed Feb. 15, 2002 (Now U.S. Pat. No. 7,691,804), which is a continuation of International Application No. PCT/US00/22507, filed Aug. 16, 2000, which claims the benefit of U.S. Provisional Application No. 60/183,536, filed Feb. 18, 2000, U.S. Provisional Application No. 60/181,684, filed Feb. 11, 2000 and U.S. Provisional Application No. 60/149,378, filed Aug. 17, 1999, all of which are incorporated herein by reference.

FIELD OF THE INVENTION

The present invention relates to the use of a receptor to BAFF, a β-cell activating factor belonging to the Tumor Necrosis Factor ("TNF") family, and its blocking agents to either stimulate or inhibit the expression of B-cells and immunoglobulins. This receptor has anti-cancer and immunoregulatory applications as well as uses for the treatment of immunosuppressive disorders such as HIV. In addition, the receptor and its blocking agents play a role in the development of hypertension and its related disorders. Furthermore, cells transfected with the gene for this receptor may be used in gene therapy to treat tumors, lymphomas, autoimmune diseases or inherited genetic disorders involving B-cells. Blocking agents, such as recombinant variants or antibodies specific to the receptor, have immunoregulatory applications as well. Use of the receptor to BAFF as a B-cell stimulator for immune suppressed diseases including for example uses for patients undergoing organ transplantation (e.g., bone marrow transplant) as well as recovering from cancer treatments to stimulate production of B cells are contemplated. Use of the receptor to BAFF as an adjuvant and or costimulator to boost and/or restore B cell levels to approximately normal levels are also contemplated. Soluble forms of the receptor to BAFF that block B cell function may also be used to inhibit B-cell mediated diseases.

BACKGROUND OF THE INVENTION

The present invention relates to a novel receptor in the TNF family. A novel receptor has been identified, BAFF-R (or "BCMA").

The TNF family consists of pairs of ligands and their specific receptors referred to as TNF family ligands and TNF family receptors (Bazzoni and Beutler, 1996). The family is involved in the regulation of the immune system and possibly other non-immunological systems. The regulation is often at a "master switch" level such that TNF family signaling can result in a large number of subsequent events best typified by TNF. TNF can initiate the general protective inflammatory response of an organism to foreign invasion that involves the altered display of adhesion molecules involved in cell trafficking, chemokine production to drive specific cells into specific compartments, and the priming of various effector cells. As such, the regulation of these pathways has clinical potential.

Induction of various cellular responses mediated by such TNF family cytokines is believed to be initiated by their binding to specific cell receptors. At least two distinct TNF receptors of approximately 55 kDa (TNFR1) and 75 kDa (TNFR2) have been identified [Hohman et al., J. Biol. Chem. 264: 14927-14934 (1989) and Brockhaus et al., PNAS, 87: 3127-3131 (1990)]. Extensive polymorphisms have been associated with both TNF receptor genes. Both TNFRs share the typical structure of cell surface receptors including extracellular, transmembrane and intracellular domains. The extracellular portion of type 1 and type 2 TNFRs contains a repetitive amino acid sequence pattern of four cysteine rich domains (CDRs). A similar repetitive pattern of CDRs exist in several other cell surface proteins, including p75 nerve growth factor receptor, the B-cell antigen CD40 amongst others.

The receptors are powerful tools to elucidate biological pathways because of their easy conversion to immunoglobulin fusion proteins. These dimeric soluble receptor forms are good inhibitors of events mediated by either secreted or surface bound ligands. By binding to these ligands they prevent the ligand from interacting with cell associated receptors that can signal. Not only are these receptor-Ig fusion proteins useful in an experimental sense, but they have been successfully used clinically in the case of TNF-R-Ig to treat inflammatory bowel disease, rheumatoid arthritis and the acute clinical syndrome accompanying OKT3 administration (Eason et al., 1996; Feldmann et al., 1996; van Dullemen et al., 1995). One can envision that manipulation of the many events mediated by signaling through the TNF family of receptors will have wide application in the treatment of immune based diseases and also the wide range of human diseases that have pathological sequelae due to immune system involvement. A soluble form of a recently described receptor, osteoprotegerin, can block the loss of bone mass and, therefore, the events controlled by TNF family receptor signaling are not necessarily limited to immune system regulation. Antibodies to the receptor can block ligand binding and hence can also have clinical application. Such antibodies are often very long-lived and may have advantages over soluble receptor-Ig fusion proteins which have shorter blood half-lives.

While inhibition of the receptor mediated pathway represents the most exploited therapeutic application of these receptors, originally it was the activation of the TNF receptors that showed clinical promise (Aggarwal and Natarajan, 1996). Activation of the TNF receptors can initiate cell death in the target cell and hence the application to tumors was and still is attractive (Eggermont et al., 1996). The receptor can be activated either by administration of the ligand, i.e. the natural pathway or some antibodies that can crosslink the receptor are also potent agonists. Antibodies would have an advantage in oncology since they can persist in the blood for long periods whereas the ligands generally have short lifespans in the blood. As many of these receptors may be expressed more selectively in tumors or they may only signal cell death or differentiation in tumors, agonist antibodies could be good weapons in the treatment of cancer. Likewise, many positive immunological events are mediated via the TNF family receptors, e.g. host inflammatory reactions, antibody production etc. and therefore agonistic antibodies could have beneficial effects in other, non-oncological applications.

Paradoxically, the inhibition of a pathway may have clinical benefit in the treatment of tumors. For example the Fas ligand is expressed by some tumors and this expression can lead to the death of Fas positive lymphocytes thus facilitating the ability of the tumor to evade the immune system. In this case, inhibition of the Fas system could then allow the immune system to react to the tumor in other ways now that access is possible (Green and Ware, 1997).

SUMMARY OF THE INVENTION

Applicants have identified a cDNA clone that encodes a polypeptide, designated in the present application as "BAFF- R" or as "BCMA", that binds the tumor necrosis factor, BAFF, a B-cell activating factor belonging to the Tumor Necrosis Factor ("TNF") family. BAFF is the same molecule previously described in WO/9912964, which is incorporated by reference herein.

In one embodiment, the invention provides methods of using BAFF-R. Included in such methods are methods of inhibiting B-cell growth, dendritic cell-induced B-cell growth and maturation or immunoglobulin production in an animal using BAFF-R polypeptide. Also included are methods of stimulating B-cell growth, dendritic cell-induced B-cell growth and maturation or immunoglobulin production in an animal using BAFF-R polypeptide or co-stimulating B-cell growth, dendritic cell-induced B-cell growth and maturation or immunoglobulin production in an animal using BAFF-R polypeptide and an anti-T antibody, a CD40 ligand or an anti-CD40 ligand.

In another embodiment, the invention provides methods of using BAFF-R in the treatment of autoimmune diseases, hypertension, cardiovascular disorders, renal disorders, B-cell lympho-proliferate disorders, immunosuppressive diseases, organ transplantation, and HIV. Also included are methods of using agents for treating, suppressing or altering an immune response involving a signaling pathway between BAFF-R and its ligand, and methods of inhibiting inflammation by administering an antibody specific for a BAFF-R or an epitope thereof.

The methods of the present invention are preferably carried out by administering a therapeutically effective amount of a BAFF-R polypeptide, a chimeric molecule comprising a BAFF-R polypeptide fused to a heterologous amino acid sequence, or an anti-BAFF-R antibody homolog.

In one embodiment, the invention provides pharmaceutical compositions comprising a BAFF-R polypeptide and a pharmaceutically acceptable excipient.

In another embodiment, the invention provides chimeric molecules comprising BAFF-R polypeptide fused to a heterologous polypeptide or amino acid sequence. An example of such a chimeric molecule comprises a BAFF-R fused to a Fc region of an immunoglobulin or an epitope tag sequence.

In another embodiment, the invention provides an antibody that specifically binds to a BAFF-R polypeptide. Optionally, the antibody is a monoclonal antibody.

BRIEF DESCRIPTION OF THE DRAWINGS

FIG. 6(a) shows FACS overlay of 293EBNA transfected with pJST535 and stained as follows: no ligand (black histogram), 1 ug/ml flag-hCD40L (pink) or flag-hBAFF (green). All samples were then stained with anti-flag M2 followed by donkey anti-mouse IgG as described in methods in Example 2.

FIG. 10(a) shows plots of expression of IgM vs. CD 1 in a FACS analysis for Baff Tg mice that received h-Ig (middle panel) or hBCMA-Ig (lower panel) and for wildtype littermate controls that received PBS injections (upper panel), as described in Example 11.

FIG. 10(b) shows plots of expression of CD21 vs. IgM in FACS analysis by gating on IgD positive populations for Baff Tg mice that received h-Ig (middle panel) or hBCMA-Ig (lower panel) and for wildtype littermate controls that received PBS injections (upper panel), as described in Example 11.

DETAILED DESCRIPTION

I. Definitions

Figures 1, 2:
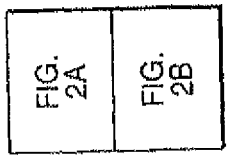
FIG. 1 shows the nucleic acid sequence (SEQ ID NO:2) of a cDNA for human BAFF-R (BCMA) and its derived amino acid sequence (SEQ ID NO:1). Potential start of translation at either nucleic acid residue 219 or 228; cysteine rich domain (CRD) at nucleic acid residues 240-341 of SEQ ID NO: 2 (amino acid residues 8-41 of SEQ ID NO:1); and potential transmembrane region at nucleic acid residues 375-459 of SEQ ID NO:2.
FIG. 2 shows the nucleic acid sequence (SEQ ID NO: 4) and its derived amino acid sequence (SEQ ID NO:3) of pJST538, a plasmid encoding BAFF-R-Fc: nucleic acid residues 1-69, murine IgG-kappa signal sequence; nucleic acid residues 70-222, BAFF-R (nucleic acid residues 1-153); nucleic acid residues 223-906, human IgG.
Figure 4:
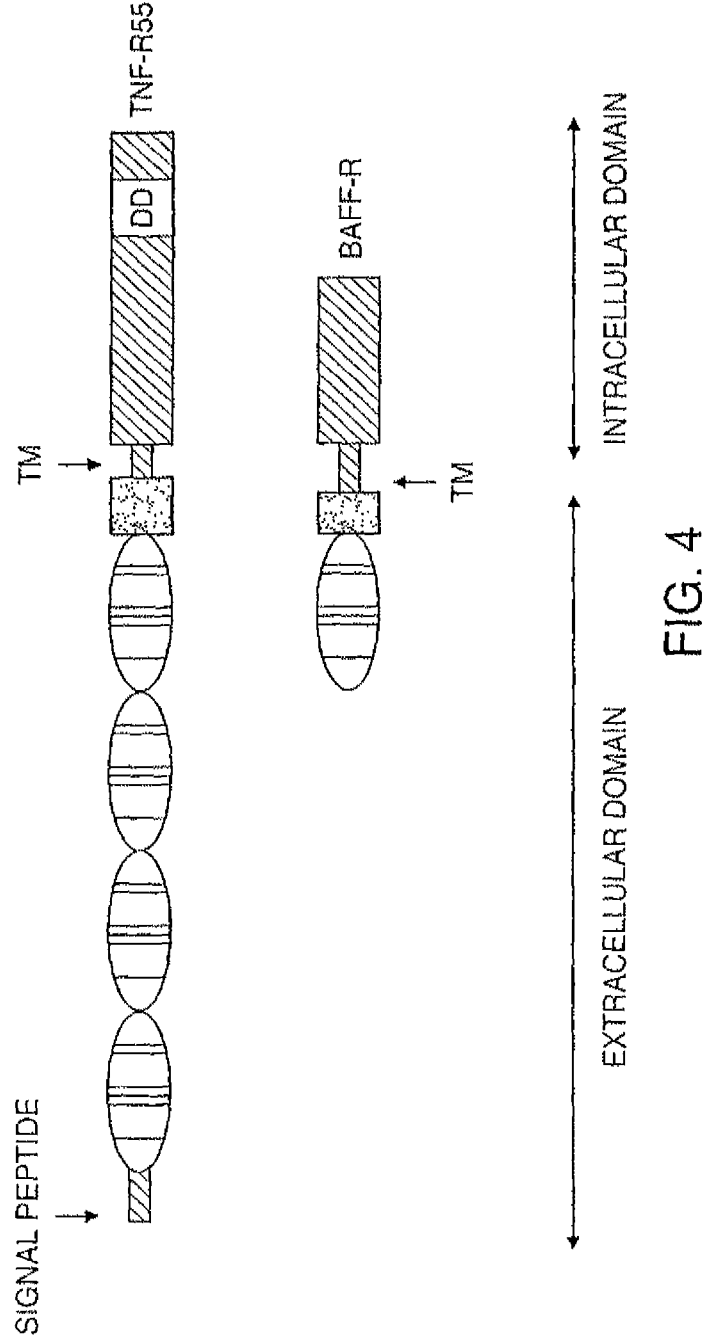
FIG. 4 shows a structure comparison between TNF-R55 and BAFF-R.
Figure 5A:
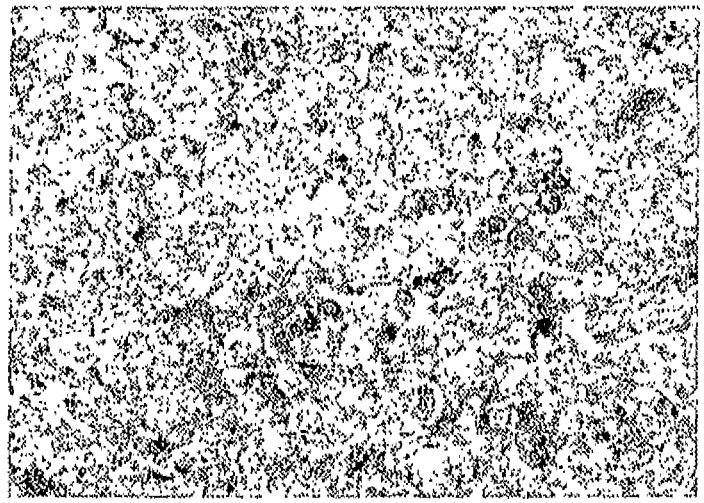
FIG. 5 shows 293EBNA cells transfected with either (a) CH269 (1.0 ug) or (b) pJST535 (0.1 ug), the plasmid expressing full length BAFF-R, and stained with 0.5 ug/ml flag-hBAFF in the plate assay format.
Figure 5B:
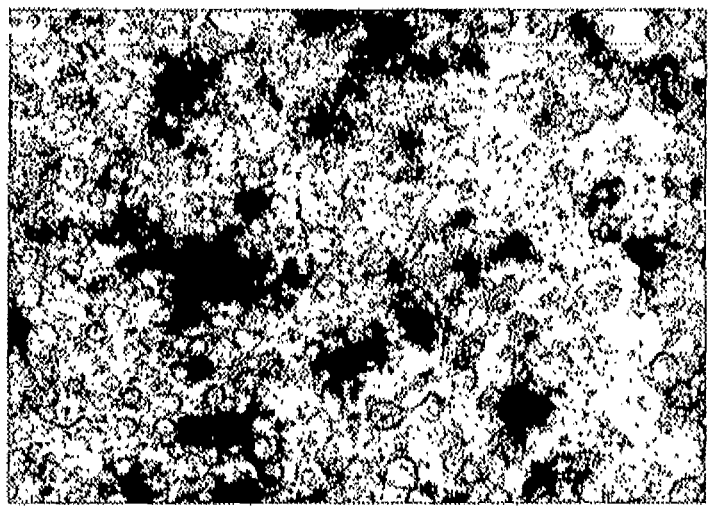

The terms "BAFF-R" and "BCMA" when used herein encompass native sequence BAFF-R and BAFF-R variants (which are further defined herein). The BAFF-R may be isolated from a variety of sources, such as from murine or human tissue types or from another source, or prepared by recombinant or synthetic methods.

A "native sequence BAFF-R" comprises a polypeptide having the same amino acid sequence as BAFF-R derived from nature. Such native sequence BAFF-R can be isolated from nature or can be produce by recombinant or synthetic means. The naturally-occurring truncated or secreted forms of the BAFF-R (e.g. soluble forms containing for instance, an extracellular domain sequence), naturally-occurring variant forms (e.g., alternatively spliced forms) and naturally-occurring allelic variants of the BAFF-R. In one embodiment of the invention, the native sequence BAFF-R is a mature or full-length native sequence BAFF-R polypeptide comprising amino acids 1 to 184 of SEQ ID NO: 1 or fragment thereof.

The "BAFF-R extracellular domain" or "BAFF-R ECD" refers to a form of BAFF-R which is essentially free of transmembrane and cytoplasmic domains of BAFF-R. Ordinarily, BAFF-R extracellular domain will have less than 1% of such transmembrane and cytoplasmic domains and will preferably have less than 0.5% of such domains. Optionally, BAFF-R ECD will comprise amino acid residues 8 to 41 of SEQ ID NO:1, or amino acid residues 4 to 51 of SEQ ID NO: 1, or amino acid residues 1 to 53 of SEQ ID NO: 1. In a preferred embodiment of the present invention, the BAFF-R ECD comprises amino acid residues 1 to 51 of SEQ ID NO: 1. It will be understood by the skilled artisan that the transmembrane domain identified for the BAFF-R polypeptide of the present invention is identified pursuant to criteria routinely employed in the art for identifying that type of hydrophobic domain. The exact boundaries of a transmembrane domain may vary but most likely by no more than about 5 amino acids at either end of the domain specifically mentioned herein. Accordingly, the BAFF-R ECD may optionally comprise amino acids 8-41 (SEQ ID NO:1).

"BAFF-R variant" means an active BAFF-R as defined below having at least about 80% amino acid sequence identity with the BAFF-R having the deduced amino acid sequence shown in SEQ ID NO:1 for a full-length native sequence BAFF-R or with a BAFF-R ECD sequence. Such BAFF-R variants include, for instance, BAFF-R polypeptides wherein one or more amino acid residues are added, or deleted, at the end or C-terminus of the sequence of SEQ ID NO:1. Ordinarily, a BAFF-R variant will have at least about 80% or 85% amino acid sequence identity, more preferably at least about 90% amino acid sequence identity, and even more preferably at least about 95% amino acid sequence identity with the amino acid sequence of SEQ ID NO:1.

"Percent (%) amino acid sequence identity" with respect BAFF-R sequences identified herein is defined as the percentage of amino acid residues in a candidate sequence that are identical with the amino acid residues in the BAFF-R sequence, after is aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The term "epitope tagged" when used herein refers to a chimeric polypeptide comprising BAFF-R, or a domain sequence thereof, fused to a "tag polypeptide". The tag polypeptide has enough residues to provide an epitope against which an antibody can be made, or which can be identified by some other agent, yet is short enough so that it does not interfere with activity of the BAFF-R. The tag polypeptide preferably also is fairly unique so that the antibody does not substantially cross-react with other epitopes. Suitable tag polypeptides generally have at least 6 amino acid residues and usually between about 8 to about 50 amino acid residues (preferably, about 10 to about 20 residues).

"Isolated" when used to describe the various polypeptides disclosed herein, means polypeptide that has been identified and separated and/or recovered from a component of its natural environment. Contaminate components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity SDSPAGE under non-reducing or reducing conditions using Coomassie blue or preferably, silver stain. Isolated polypeptide includes polypeptide in situ within recombinant cells, since at least one component of the BAFF-R's natural environment will not be present. Ordinarily, however, isolated polypeptide will be prepared by at least one purification step.

The term "antibody" is used in the broadest sense and specifically covers single BAFF-R monoclonal antibodies (including agonist, antagonist, and neutralizing antibodies) and anti-BAFF-R antibody compositions with polyepitopic specificity. The term "monoclonal antibody" as used herein refers to an antibody obtained from a population of substantially homogeneous antibodies, i.e. the individual antibodies comprising the population are identical except for possible naturally-occurring mutations that may be present in minor amounts.

A "purified preparation" or a "substantially pure preparation" of a polypeptide, as used herein, means a polypeptide that has been separated from other proteins, lipids, and nucleic acids with which it naturally occurs. Preferably, the polypeptide is also separated from other substances, e.g., antibodies, matrices, etc., which are used to purify it.

The terms, "treating", "treatment" and "therapy" as used herein refers to curative therapy, prophylactic therapy, and preventative therapy.

The terms "peptides", "proteins", and "polypeptides" are used interchangeably herein.

"Biologically active" as used herein, means having an in vivo or in vitro activity which may be performed directly or indirectly. Biologically active fragments of BAFF-R may have, for example, 70% amino acid homology with the active site of the receptor, more preferably at least 80%, and most preferably, at least 90% homology. Identity or homology with respect to the receptor is defined herein as the percentage of amino acid residues in the candidate sequence which are identical to the BAFF-R residues in SEQ ID NO: 1, or which are identical to a defined portion of the amino acid residues in SEQ ID NO:1.

The term "mammal" as used herein refers to any animal classified as a mammal including humans, cows, horses, dogs, mice and cats. In preferred embodiment of the invention, the mammal is a human.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature.

Reference will now be made in detail to the present preferred embodiments of the invention. This invention relates to the use of BAFF-R and BAFF-R related molecules to effect the growth and maturation of B-cells and the secretion of immunoglobulin. The invention relates to the use of BAFF-R and BAFF-R related molecules to effect responses of the immune system, as necessitated by immune-related disorders. Additionally, this invention encompasses the treatment of cancer and immune disorders through the use of a BAFF-R, or BAFF-R related gene through gene therapy methods.

The BAFF-R and homologs thereof produced by hosts transformed with the sequences of the invention, as well as native BAFF-R purified by the processes known in the art, or produced from known amino acid sequences, are useful in a variety of methods for anticancer, antitumor and immunoregulatory applications. They are also useful in therapy and methods directed to other diseases.

Another aspect of the invention relates to the use of the polypeptide encoded by the isolated nucleic acid encoding the BAFF-R in "antisense" therapy. As used herein, "antisense" therapy refers to administration or in situ generation of oligonucleotides or their derivatives which specifically hybridize under cellular conditions with the cellular mRNA and/or DNA encoding the ligand of interest, so as to inhibit expression of the encoded protein, i.e. by inhibiting transcription and/or translation. The binding may be by conventional base pair complementarity, or, for example, in the case of binding to DNA duplexes, through specific interactions in the major groove of the double helix. In general, "antisense" therapy refers to a range of techniques generally employed in the art, and includes any therapy which relies on specific binding to oligonucleotide sequences.

An antisense construct of the present invention can be delivered, for example, as an expression plasmid, which, when transcribed in the cell, produces RNA which is complementary to at least a portion of the cellular mRNA which encodes BAFF-ligand. Alternatively, the antisense construct can be an oligonucleotide probe which is generated ex vivo. Such oligonucleotide probes are preferably modified oligonucleotides which are resistant to endogenous nucleases, and are therefor stable in vivo. Exemplary nucleic acids molecules for use as antisense oligonucleotides are phosphoramidates, phosphothioate and methylphosphonate analogs of DNA (See, e.g., U.S. Pat. Nos. 5,176,996; 5,264,564; and 5,256,775). Additionally, general approaches to constructing oligomers useful in antisense therapy have been reviewed, for example, by Van Der Krol et al., (1988) Biotechniques 6:958-976; and Stein et at (1988) Cancer Res 48: 2659-2668, specifically incorporated herein by reference.

The BAFF-R of the invention, as discussed above, is a member of the TNF receptor family. The protein, fragments or homologs thereof may have wide therapeutic and diagnostic applications.

The polypeptides of the invention specifically interact with BAFF, a polypeptide previously described in WO99/12964 incorporated by reference herein. However, the peptides and methods disclosed herein enable the identification of molecules which specifically interact with the BAFF-R or fragments thereof.

The claimed invention in certain embodiments includes methods of using peptides derived from BAFF-R which have the ability to bind to BAFF. Fragments of the BAFF-Rs can be produced in several ways, e.g., recombinantly, by PCR, proteolytic digestion or by chemical synthesis. Internal or terminal fragments of a polypeptide can be generated by removing one or more nucleotides from one end or both ends of a nucleic acid which encodes the polypeptide. Expression of the mutagenized DNA produces polypeptide fragments.

Chimeric molecules for use in the present invention can also be produced using techniques known in the art. The present invention contemplates the use of chimeric molecules comprising a BAFF-R polypeptide (or variant thereof) fused to a heterologous amino acid sequence, such as the IgG Fc domain of an immunoglobulin. Preferably, such chimeric molecules are soluble and comprise a soluble BAFF-R polypeptide.

Polypeptide fragments can also be chemically synthesized using techniques known in the art such as conventional Merrifield solid phase f-moc or t-boc chemistry. For example, peptides and DNA sequences of the present invention may be arbitrarily divided into fragments of desired length with no overlap of the fragment, or divided into overlapping fragments of a desired length. Methods such as these are described in more detail below.

Generation of Soluble Forms of BAFF-R

Soluble forms of the BAFF-R can often signal effectively and hence can be administered as a drug which now mimics the natural membrane form. It is possible that the BAFF-R claimed herein are naturally secreted as soluble cytokines, however, if not, one can reengineer the gene to force secretion. To create a soluble secreted form of BAFF-R, one would remove at the DNA level the N-terminus transmembrane regions, and some portion of the stalk region, and replace them with a type I leader or alternatively a type II leader sequence that will allow efficient proteolytic cleavage in the chosen expression system. A skilled artisan could vary the amount of the stalk region retained in the secretion expression construct to optimize both ligand binding properties and secretion efficiency. For example, the constructs containing all possible stalk lengths, i.e. N-terminal truncations, could be prepared such that proteins starting at amino acids 1 to 51 would result. The optimal length stalk sequence would result from this type of analysis.

In preferred embodiments of the present invention, the soluble BAFF-R polypeptide is: an isolated native sequence BAFF-R polypeptide comprising amino acid residues 1 to 51 of SEQ NO:1 or a fragment thereof; an isolated BAFF-R polypeptide having at least 80% (and more preferably 90%) amino acid sequence identity with native sequence BAFF-R polypeptide comprising amino acid residues 1 to 51 of SEQ ID NO: 1 or a fragment thereof; or an isolated BAFF-R polypeptide comprising amino acid residues 8 to 41 of SEQ ID NO: 1 or a fragment thereof.

Generation of Antibodies Reactive with the BAFF-R

The invention also includes antibodies specifically reactive with the claimed BAFF-R or its co-receptors. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers, or other techniques, well known in the art.

An immunogenic portion of BAFF-R or its co-receptors can be administered in the presence of an adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of BAFF-R or its co-receptors, e.g. antigenic determinants of a polypeptide of SEQ ID NO:1, or a closely related human or non-human mammalian homolog (e.g. 70, 80 or 90 percent homologous, more preferably at least 95 percent homologous). In yet a further preferred embodiment of the present invention, the anti-BAFF-R or anti-BAFF-co-receptor antibodies do not substantially cross react (i.e. react specifically) with a protein which is e.g., less than 80 percent homologous to SEQ ID NO:1; preferably less than 90 percent homologous with SEQ ID NO: 1; and, most preferably less than 95 percent homologous with SEQ ID NO:1. By "not substantially cross react", it is meant that the antibody has a binding affinity for a non-homologous protein which is less than 10 percent, more preferably less than 5 percent, and even more preferably less than 1 percent, of the binding affinity for a protein of SEQ ID NO: 1.

The term antibody as used herein is intended to include fragments thereof which are also specifically reactive with BAFF-R, or its receptors. Antibodies can be fragmented using conventional techniques and the fragments screened for utility in the same manner as described above for whole antibodies. For example, $F(ab')_2$ fragments can be generated by treating antibody with pepsin. The resulting $F(ab)_2$ fragment can be treated to reduce disulfide bridges to produce Fab' fragments. The antibodies of the present invention are further intended to include biospecific and chimeric molecules having anti-BAFF-R or anti-BAFF-co-receptor activity. Thus, both monoclonal and polyclonal antibodies (Ab) directed against BAFF-R, and their co-receptors, and antibody fragments such as Fab' and $F(ab')_2$, can be used to block the action of the BAFF-R and its respective co-receptors.

Various forms of antibodies can also be made using standard recombinant DNA techniques. (Winter and Milstein, Nature 349: 293-299 (1991) specifically incorporated by reference herein.) For example, chimeric antibodies can be constructed in which the antigen binding domain from an animal antibody is linked to a human constant domain (e.g. Cabilly et al., U.S. Pat. No. 4,816,567, incorporated herein by reference). Chimeric antibodies may reduce the observed immunogenic responses elicited by animal antibodies when used in human clinical treatments.

In addition, recombinant "humanized antibodies" which recognize BAFF-R or its co-receptors can be synthesized. Humanized antibodies are chimeras comprising mostly to human IgG sequences into which the regions responsible for specific antigen-binding have been inserted. Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (i.e. inter species) sequences in human antibodies, and thus are less likely to elicit immune responses in the treated subject.

Construction of different classes of recombinant antibodies can also be accomplished by making chimeric or humanized antibodies comprising variable domains and human constant domains (CH1, CH2, CH3) isolated from different classes of immunoglobulins. For example, antibodies with increased antigen binding site valencies can be recombinantly produced by cloning the antigen binding site into vectors carrying the human: chain constant regions. (Arulanandam et al., J. Exp. Med., 177: 1439-1450 (1993), incorporated herein by reference.)

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling. (Queen et al., Proc. Natl. Acad. Sci. 86: 10029-33 (1989) incorporated herein by reference.

Generation of Analogs: Production of Altered DNA and Peptide Sequences

Analogs of the BAFF-R can differ from the naturally occurring BAFF-R in amino acid sequence, or in ways that do not involve sequence, or both. Non-sequence modifications include in vivo or in vitro chemical derivatization of the BAFF-R. Non-sequence modifications include, but are not limited to, changes in acetylation, methylation, phosphorylation, carboxylation or glycosylation.

Preferred analogs include BAFF-R biologically active fragments thereof, whose sequences differ from the sequence given in SEQ ID NO: 1, by one or more conservative amino acid substitutions, or by one or more non-conservative amino acid substitutions, deletions or insertions which do not abolish the activity of BAFF-ligand. Conservative substitutions typically include the substitution of one amino acid for another with similar characteristics, e.g. substitutions within the following groups: valine, glycine; glycine, alanine; valine, isoleucine, leucine; aspartic acid, glutamic acid; asparagine, glutamine; serine, threonine; lysine, arginine; and, phenylalanine, tyrosine.

Uses

The full length BAFF-R gene (SEQ ID NO: 2) or portions thereof may be used as hybridization probes for a cDNA library to isolate, for instance, still other genes which have a desired sequence identity to the BAFF-R sequence disclosed in SEQ ID NO: 2. Nucleotide sequences encoding BAFF-R can also be used to construct hybridization probes for mapping the gene which encodes the BAFF-R and for the genetic analysis of individuals with genetic disorders. Screening assays can be designed to find lead compounds that mimic the biological activity of a BAFF-R. Such screening assays will include assays amenable to high-throughput screening of chemical libraries, making them particularly suitable for identifying small molecule drug candidates. Small molecules contemplated include synthetic organic or inorganic compounds. Nucleic acids which encode BAFF-R or its modified forms can also be used to generate either transgenic animals or "knock out" animals which in turn are useful in the development and screening of therapeutically useful reagents.

As described herein, in one embodiment of the invention, there are provided methods of stimulating B-cell growth, dendritic cell-induced B-cell growth and maturation or immunoglobulin production in an animal using BAFF-R polypeptide or co-stimulating B-cell growth, dendritic cell-induced B-cell growth and maturation or immunoglobulin production in an animal using BAFF-R polypeptide and an anti-T antibody, a CD40 ligand or an anti-CD40 ligand. Also included are methods of inhibiting B-cell growth, dendritic cell-induced B-cell growth and maturation or immunoglobulin production in an animal using BAFF-R polypeptide.

In another embodiment, the invention provides methods of using BAFF-R in the treatment of autoimmune diseases, hypertension, cardiovascular disorders, renal disorders, B-cell lympho-proliferate disorders, immunosuppressive diseases, organ transplantation, inflammation, and HIV. Also included are methods of using agents for treating, suppressing or altering an immune response involving a signaling pathway between BAFF-R and its ligand.

In one embodiment, the invention provides pharmaceutical compositions comprising a BAFF-R polypeptide and a pharmaceutically acceptable excipient. Suitable carriers for a BAFF-R polypeptide, for instance, and their formulations, are described in *Remington' Pharmaceutical Sciences, 16th* ed., 1980, Mack Publishing Co., edited by Oslo et al. Typically an appropriate amount of a pharmaceutically acceptable salt is used in the formulation to render the formulation isotonic. Examples of the carrier include buffers such as saline, Ringer's solution and dextrose solution. The pH of the solution is preferably from about 5 to about 8, and more preferably from about 7.4 to about 7.8. Further carriers include sustained release preparations such as semipermeable matrices of solid hydrophobic polymers, which matrices are in the form of shaped articles, e.g. liposomes, films or microparticles. It will be apparent to those of skill in the art that certain carriers may be more preferable depending upon for instance the route of administration and concentration of the a BAFF-R polypeptide being administered.

Administration may be accomplished by injection (eg intravenous, intraperitoneal, subcutaneous, intramuscular) or by other methods such as infusion that ensure delivery to the bloodstream in an effective form.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, *Molecular Cloning: A Laboratory Manual*, 2nd edition. (Sambrook, Fritsch and Maniatis, eds.), Cold Spring Harbor Laboratory Press, 1989; *DNA Cloning*, Volumes 1 and 11 (D. N. Glover, ed), 1985; *Oligonucleotide Synthesis*, (M. J. Gait, ed.), 1984; U.S. Pat. No. 4,683,195 (Mullis et al.,); *Nucleic Acid Hybridization* (B. D. Hames and S. J. Higgins, eds.), 1984; Transcription and Translation (B. D. Hames and S. J. Higgins, eds.), 1984; *Culture of Animal Cells* (R. I. Freshney, ed). Man R. Liss, Inc., 1987; *Immobilized Cells and Enzymes*, IRL Press, 1986; *A Practical Guide to Molecular Cloning* (B. Perbal), 1984; *Methods in Enzymology*, Volumes 154 and 155 (Wu et al., eds), Academic Press, New York; *Gene Transfer Vectors for Mammalian Cells* (J. H. Miller and M. P. Calos, eds.), 1987, Cold Spring Harbor Laboratory; *Immunochemical Methods in Cell and Molecular Biology* (Mayer and Walker, eds.), Academic Press, London, 1987; *Handbook of Experiment Immunology*, Volumes I-IV (D. M. Weir and C. C. Blackwell, eds.), 1986; *Manipulating the Mouse Embryo*, Cold Spring Harbor Laboratory Press, 1986.

The following Examples are provided to illustrate the present invention, and should not be construed as limiting thereof.

EXAMPLES

Example 1

Detection of BAFF Binding to BAFF-R Using a Plate Assay

In this example, the binding of BAFF to BAFF-R transfected cells using a plate assay is described.

Full-length human BAFF-R was generated from BJAB polyA+ RNA using the SuperscriptII preamplification kit (Life Technologies) to generate the cDNA template and amplified by Pfu1 using primers complementary to the 5' and 3' coding sequences of BAFF-R. The PCR product was cloned into CH269, a derivative of pCEP4 (Invitrogen). The resultant clone was termed pJST535. Human embryonic kidney cells containing the EBNA-1 gene (293EBNA) were seeded into 6 well plates coated with fibronectin and transfected by lipofectamine (Life Technologies) with either pJST535 at various dilutions or CH269 as a background control. At 48 hrs post transfection, transfected cells were assayed for their ability to bind soluble flag-hBAFF (amino acids L83-L285) as follows. All incubations were at room temperature. Conditioned media was aspirated from the wells and the cells washed with BHA buffer (20 mM HEPES pH 17.0, 0.5 mg/ml BSA, 0.1% NaN3) and incubated with 0.5 ug/ml FLAG-hBAFF diluted in PBS containing 1 mM $MgCl_2$, 1 mM $CaCl_2$ and 0.1% NaN3. After an 1 hr, incubation, the BAFF solution was removed and the cells were washed with BHA. The cells were next incubated for 30 min. in a PBS solution containing 1 ug/ml of the anti-FLAG monoclonal antibody, M2 (Sigma). This solution was aspirated and the cells were washed with BHA. The cells were then incubated for 30 min. in a 1:3000 dilution of the alkaline phosphatase conjugated goat anti-mouse IgG F(ab)'2 (Jackson ImmunoResearch). This solution was aspirated and the cells washed with BHA. To reduce the amount of background staining due to endogenous alkaline phosphatase, the cells were incubated for 15 min. in 2.5 mM levamisol (Vector Laboratories) diluted in 100 mM NaCl, 100 mM Tris-Cl pH9.5 and 5 mM $MgCl_2$. For chromogenic detection of alkaline phosphatase, the inhibitor solution was aspirated and the cells were incubated with a solution of fast red and napthol phosphate (Pierce). Staining was observed and photographed through a low power microscope.

The deposition of fast red dye was observed for all the wells transfected with the BAFF-R expressing plasmid, pJST535. The frequency of the signal titrated away as the amount of plasmid transfected into the cells decreased. No staining was observed for the control expression vector, CH269, transfected cells. Also, no staining was observed on any of the transfected cells when FLAG-hBAFF was omitted from the staining protocol or when another TNF family member ligand, FLAG-tagged LIGHT, was substituted for flag-hBAFF. Therefore the staining of BAFF-R transfected cells with BAFF appears specific.

Example 2

BAFF Binding to BAFF-R Transfected Cells by FACS Analysis

This example describes the detection of BAFF to BAFF-R transfected cells using FACS analysis.

The plasmid encoding full-length BAFF-R, pJST535, was transfected into 293EBNA cells using FuGene6 (Boehringer Mannheim). At 24 or 48 hr post transfection, cells were removed from the plates using 5 mM EDTA in PBS and counted. The cells were washed twice with FACS buffer (PBS containing 10% fetal bovine serum, 0.1% NaN3 and 10 ug/ml hIgG (Jackson ImmunoResearch) and then $2.5 \times 10^5$ cells were incubated for 1 hr on ice with FLAG-hBAFF diluted into FACS buffer at concentrations ranging from 9 ug/ml to 0.037 ug/ml. The cells were washed with FACS buffer and incubated with the anti-FLAG monoclonal antibody, M2, at 5 ug/ml for 30 min. on ice. The cells were washed with FACS buffer and incubated for 30 min. on ice in a solution containing a 1:100 dilution of R-phycoerythrin conjugated F(ab')2 donkey anti-mouse IgG and 10 ug/ml 7-AAD. After the cells were washed with FACS buffer, they were resuspended in FACS buffer containing 1% paraformaldehyde. FACS analysis followed where the 7-AAD positive (dead) cells were gated out.

The results of the FACS analysis indicate that a fraction of the cells that were transfected with BAFF-R are able to bind BAIT. At a BAFF concentration of 9 ug/ml, about 28% of the cells bind BAFF for a mean fluorescence intensity (MFI) of 366. Using the PE-labeled donkey anti-mouse reagent alone, there is not a significant shift of the cells. Only 1.3% of the cells have a MFI of 23.5 with the average of all the cells being 5.5. The signal on the BAFF-R transfected cells titrates out with decreasing amounts of BAFF. At 100 ng/ml, 8.76% of the cells have an MFI of 78.9.

Example 3

FACS Analysis of BAFF/BAFF-R Interaction Including a GFP Marker

In this example, the ability of BAFF to bind to cells co-transfected with BAFF-R and a GFP reporter plasmid is described.

The 293EBNA cells were transfected with pJST535 and a GFP reporter plasmid, as described in example 2. The reporter plasmid encodes a membrane anchored GFP molecule. Using co-transfection of the two plasmids, we analyzed the percentage of transfected cells which were capable of binding BAFF. The cells were removed from the plates and subjected to BAFF binding and detection as described in example 2. Again, 7-AAD was included in order to gate out the dead cells. The samples were analyzed by FACS and plotted. The upper right quadrant represents cells with bound BAFF (phycoerythrin positive) and expressing GFP.

Although not all of the GFP transfected cells appear to bind BAFF, there is a significant fraction of the cells in the upper right quadrant compared to the control. Thirty-three percent of the transfected cells are in the upper right compared to 8 percent It may be that a certain level of BAFF-R expression is required for BAFF to bind to the cells. It is also possible that a co-receptor is required for a high affinity interaction and that this receptor is limiting on the 293EBNA cells.

Example 4

Immunoprecipitation of Flag-hBAFF by BAFF-R-Fc Fusion

This example describes specific interaction of flag-hBAFF with BAFF-R-Fc, a molecule composed of the Cysteine Rich Domain (CRD) of BAFF-R fused to the Fc domain of human IgG 1.

The CRD of BAFF-R was generated by RT-PCR from BJAB polyA+ RNA as in Example 1 using as a 3' primer an oligo complementary to nucleotides 132-152 of the hBAFF-R coding sequence. The resultant PCR fragment was cloned in CH269 downstream of a murine IgG-kappa signal sequence and upstream of the Fc moiety of human IgG. This construct was termed pJST538. The construct pJST538 or CH269 were transfected to 293EBNA by lipofectamine. Conditioned media and cell extracts were harvested at 20 hours post transfection. Cells were solubilzed in 20 mM Tris pH7.5/50 mM Nacl/0.5% NP40/0.5% deoxycholic acid and debris spun out. An aliquot of the conditioned media and cell extracts were combined with an equal volume 2×SDS reducing buffer, boiled and subjected to SDS-PAGE and Western transfer. To verify expression, the membrane was probed with 1:3000 dilution of mouse anti-human IgG conjugated to horse radish peroxidase (HRP) in 5% nonfat dry milk in TBST at room temperature for 30 minutes and washed with TBST. Blots were developed with ECL (Amersham) and exposed to film.

Immunoprecipitations were performed by incubating 25 ng of either flag-hBAFF or flag-hTWEAK with 0.5 ml of conditioned media from 293EBNA transfected with either pJST538 or CH269 at 4° C. for 1 hour with agitation followed by the addition of 30 ul ProteinA-Sepharose (Pharmacia) and continued agitation overnight. ProteinA-Sepharose beads were washed twice with PBS and resuspended in 2×SDS reducing sample buffer. After SDS-PAGE and western transfer, the blots were incubated with 5 µg/ml anti-flag monoclonal antibody M2 (Sigma) in 5% nonfat dry milk in TBST at room temperature for 1 hour. Blots washed with TBST and incubated with a 1:3000 dilution of goat anti-mouse IgG HRP conjugate (Jackson Immunoresearch) in 5% nonfat dry milk in TBST at room temperature for 30 minutes. Blots were developed with ECL (Amersham) and exposed to film.

Upon transfection of pJST538 to 293EBNA cells, expression of an approximately 43 kDa protein was detected in both the cell extract and conditioned medium by Western blot analysis with mouse anti-human IgG (Jackson Immunoresearch), indicating that the BAFF-R-Fc fusion was efficiently expressed and secreted.

In the immunoprecipitations a band was observed only as a result of the incubation of BAFF-R-Fc and flag-hBAFF. This band co-migrated with a directly loaded sample of flag-hBAFF. None of the other lanes produced a signal, indicating that the interaction between BAFF-R-Fc and flag-hBAFF is specific.

Example 5

Generation of Soluble Receptor Forms

To form an receptor inhibitor for use in man, one requires the human receptor cDNA sequence of the extracellular domain. If the mouse form is known, human cDNA libraries are screened using the mouse cDNA sequence and such manipulations are routinely carried out in this area. With a human cDNA sequence, one can design oligonucleotide primers to PCR amplify the extracellular domain of the receptor in the absence of the transmembrane and intracellular domains. Typically, one includes most of the amino acids between the last disulfide linked "TNF domain" and the transmembrane domain. One can vary the amount of "stalk" region included to optimize the potency of the resultant soluble receptor. This amplified piece would be engineered to include suitable restriction sites to allow cloning into various C-terminal Ig fusion chimera vectors. Alternatively, one can insert a stop signal at the 3' end and make a soluble form of the receptor without resorting to the use of a Ig fusion chimera approach. The resultant vectors can be expressed in most systems used in biotechnology including yeast, insect cells, bacteria and mammalian cells and examples exist for all types of expression. Various human Fc domains can be attached to optimize or eliminate FcR and complement interactions as desired. Alternatively, mutated forms of these Fc domains can be used to selectively remove FcR or complement interactions or the attachment of N-linked sugars to the Fe domain which has certain advantages.

Example 6

Generation of Agonistic or Antagonistic Antibodies

The above described soluble receptor forms can be used to immunize mice and to make monoclonal antibodies by conventional methods. The resultant mAbs that are identified by ELISA methods can be further screened for agonist activity either as soluble antibodies or immobilized on plastic in various in vitro cellular assays. Often the death of the HT29 cell line is a convenient system that is sensitive to signaling through many TNF receptors. If this line does not possess the receptor of interest, that full length receptor can be stably transfected into the HT29 line to now allow the cytotoxicity assay to work. Alternatively, such cells can be used in the Cytosensor apparatus to assess whether activation of the receptor can elicit a pH change that is indicative of a signaling event. TNF family receptors signal well in such a format and this method does not require one to know the actual biological events triggered by the receptor. The agonistic mAbs would be "humanized" for clinical use. This procedure can also be used to define antagonistic mAbs. Such mAbs would be defined by the lack of agonist activity and the ability to inhibit receptor-ligand interactions as monitored by ELISA, classical binding or BIAcore techniques. Lastly, the induction of chemokine secretion by various cells in response to an agonist antibody can form a screening assay.

Example 7

Screening for Inhibitors of the Receptor-Ligand Interaction

Using the receptor-Ig fusion protein, one can screen either combinatorial libraries for molecules that can bind the receptor directly. These molecules can then be tested in an ELISA formatted assay using the receptor-Ig fusion protein and a soluble form of the ligand for the ability to inhibit the receptor-ligand interaction. This ELISA can be used directly to screen various natural product libraries etc. for inhibitory compounds. The receptor can be transfected into a cell line such as the HT29 line to form a biological assay (in this case cytotoxicity) that can then form the screening assay.

Example 8

BAFF-R-IgG Causes a Reduction in the Number of B Cells in Normal Mice

Eight-week-old female BALB/c mice were purchased from The Jackson Laboratory (Bar Harbor, Me.). Mice (3/group) received i.p. either PBS, 400 μg of human BAFF-R-huIgG1 (hBAFF-R-Ig) fusion protein (supplied by Teresa Cachero, Biogen), or 400 μg of purified human IgG (HuIgG) (Sandoz, Basel, Switzerland) on days −8, −5, −1 and +2. Mice received 100 μl of 10% sheep red blood cells (SRBC) (Colorado Serum Company, Denver, Colo.) on day 0.

At the time of sacrifice, blood was collected via cardiac puncture into tubes containing EDT, and red blood cells were lysed in a hypotonic buffer. Blood was also collected without EDTA for serum preparation. Single cell suspensions were prepared from spleens and mesenteric lymph nodes (MLN) and red blood cells were lysed in a hypotonic buffer. Flow cytometry was performed using PE-conjugated anti-CD45R/B220, anti-syndecan/CD138 and anti-B7.2, and FITC-conjugated anti-IgM and anti-CD45R/B220. All mAbs were purchased from Pharmingen (San Diego, Calif.). Briefly, Fc receptors were blocked with 10 μg/ml Fc Block (Pharmingen) for 15 min. on ice, followed by addition of PE- and FITC-conjugated mAbs and incubated on ice for 20-30 min. Cells were washed 1× and suspended in 0.5% paraformaldehyde. Cell fluorescence data were acquired on a FACSCalibur™ flow cytometer (Becton Dickinson, San Jose, Calif.) and analyzed using CELLQuest™ software (Becton Dickinson).

After treatment with hBAFF-R-Ig there was approximately a 50% reduction in the number of B cells in peripheral blood and in the peripheral lymphoid organs examined. $B220^{high}$ $IgM^{low}$ B cells accounted for 23.4% and 21.5% of cells in PBS-treated and HuIgG-treated mice, respectively, whereas this population represented only 9.9% of cells in hBAFF-R-Ig-treated mice. Plasma cells (sndecan/CD138+) appeared to be slightly decreased as well with 5.7% and 4.8% present in the blood of PBS-treated and HuIgG-treated mice, respectively, compared with 3.9% in hBAFF-R-Ig-treated mice. The B7.2 molecule was upregulated on 3.1% and 4.5% of B220+ cells in PBS-treated and HuIgG-treated mice, respectively, compared with 1.9% in hBAFF-R-Ig-treated mice.

In the spleen $B220^{high}$ B cells were markedly reduced in hBAFF-R-Ig-treated mice representing 18.8%, compared with 36.7% and 40% in PBS- and HuIgG-treated mice, respectively. This decline was observed in both $IgM^{high}$ and $IgM^{low}$ subpopulations (see Table 8A). There was no change observed in the newly formed B cell compartment in the spleen, $B220^{low}$ $IgM^{high}$ (data not shown). Plasma cells (syndecan/CD138+) appeared to be slightly decreased as well with 3.3% and 3.4% present in the spleen of PBS-treated and HuIgG-treated mice, respectively, compared with 2.4% in hBAFF-R-Ig-treated mice.

The MLN exhibited a decline in B220+ B cells with 14.1% present in hBAFF-R-Ig-treated mice compared with 26.7% and 35.8% in PBS-treated and HuIgG-treated mice, respectively. The data are summarized in Table 8A.

TABLE 8A

B cell populations in hBAFF-R-Ig, PBS and HuIgG-treated mice[1].

| Blood | $B220^{high}$ $IgM^{low}$ | Syndecan | $B7.2/B220^{low}$ |
|---|---|---|---|
| PBS | 23.4 ± 5.7 | 5.7 ± 1.5 | 3.1 ± 0.5 |
| HuIgG | 21.5 ± 4.5 | 4.8 ± 0.9 | 4.5 ± 1.0 |
| HBAFF-R-Ig | 9.9 ± 1.8 | 3.9 ± 0.6 | 1.9 ± 0.5 |

| Spleen | $B220^{high}$ $IgM^{low}$ | $B220^{high}$ $IgM^+$ | Syndecan |
|---|---|---|---|
| PBS | 27.8 ± 1.6 | 11.9 ± 1.6 | 3.3 ± 0.8 |
| HuIgG | 30.5 ± 2 | 11.8 ± 1.0 | 3.4 ± 0.7 |
| HBAFF-R-Ig | 10.6 ± 0.2 | 8.4 ± 0.2 | 2.4 ± 0.2 |

| MLN | $B220^+$ |
|---|---|
| PBS | 26.7 |
| HuIgG | 35.8 ± 3.3 |
| HBAFF-R-Ig | 14.1 ± 5.9 |

[1]The mice were treated as described in the Materials and Methods section, and the data are given as percent ± standard Deviation The decreased percentage of B7.2+ B cells in the blood and plasma cells in the blood and spleens of hBAFF-R-Ig-treated mice after immunization with SRBCs suggests that there is inhibition of B cell activation and/or maturation, and potentially increased elimination of activated B cells. A very minor percent of antigen-specific B cells would be activated and respond to any antigen, in this case SRBC. Because the hBAFF-R-Ig treatment resulted in such a dramatic reduction in the percent of B cells in all tissues examined, ~50%, the activity of hBAFF-R-Ig appears to also target resting, mature B cells.

It is therefore contemplated that BAFF-R fusion protein may be used as a therapeutic drug with clinical application in B cell-mediated diseases. Diseases include those that are autoimmune in nature such as systemic lupus erythematosus, myasthenia gravis, autoimmune hemolytic anemia, idiopathic thrombocytopenia purpura, anti-phospholipid syndrome, Chaga's disease, Grave's disease, Wegener's Granulomatosis, Poly-arteritis Nodosa and Rapidly Progressive Glomerulonephritis. The therapeutic agent also has application in plasma cell disorders such as multiple myeloma, Waldenstrom's macroglobulinemia, Heavey-chain disease, Primary or immunocyte-associated amyloidosis, and Monoclonal gammopathy of undetermined significance (MGUS). Oncology targets include B cell carcinomas, leukemias, and lymphomas.

Example 9

Blocking BAFF Induced B Cell Proliferation In Vitro Using Soluble BAFF-R

In this example we show that the soluble BAFF-R: hIgG1 fusion protein is capable of blocking BAFF induced B cell proliferation in mouse splenocytes.

Murine splenocytes ($5 \times 10^5$ cells/ml) from Balb/c mice were isolated and cultured in a 96-well plate in 100 μl of RPMI (Life Technologies) supplemented with 10% fetal calf serum (JRH), 2 mM glutamine, 100 units/ml penicillin and 100 mg/ml streptomycin (Life Technologies). Then various amounts of human BAFF, 10 μg/ml human BAFF-R: hIgG1 or human Ig, as well as 10 μg/ml of anti-mouse surface μ heavy chain (Jackson Immuno Research) were added. After 48 h in culture at 37° C., cells were pulsed for 24 h with 1 μCi/well [methyl-$^3$H]thymidine (Dupont NEN) and harvested using a Tomtec (Orange, Conn.) cell harvester. The radioactivity was measured in a Betaplate liquid scintillation counter (Pharmacia Biotech).

Figures 1, 6B:
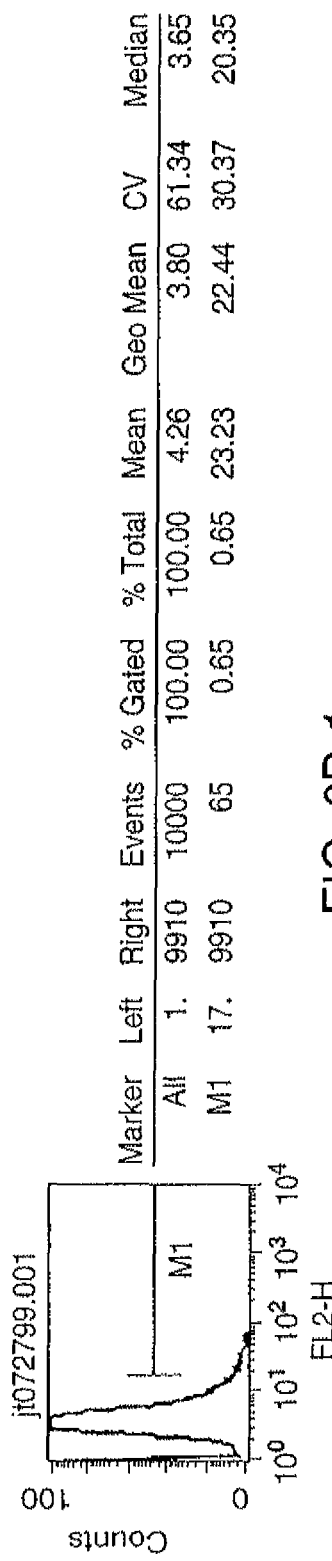
FIG. 6(b) shows FACS histograms with statistics of same experiment. Staining is as follows: (1) unstained, (2) 7AAD only, (3) $2^{nd}$ step and 7AAD only, (4) 9 ug/ml flag-hBAFF, (5) 3 ug/ml flag-hBAFF, (6) 1 ug/ml flag-hBAFF, (7) 0.33 ug/ml flag-hBAFF, (8) 0.11 ug/ml flag-hBAFF, (9) flag-hCD40L 1 ug/ml.
Figures 2, 6B:
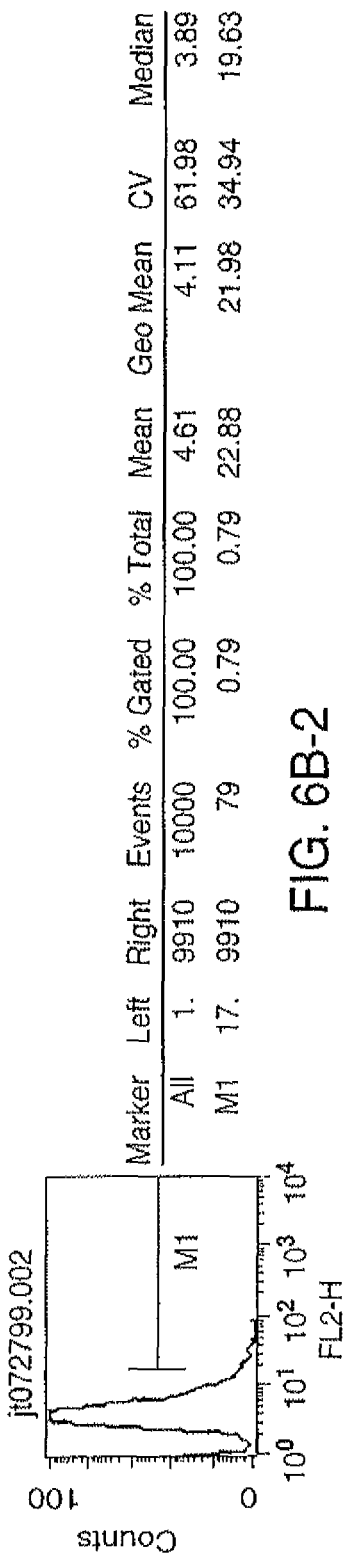
Figures 3, 6B:
FIG. 3 shows the nucleic acid sequence of pJST535, a plasmid encoding a full length human BAFF-R and its derived amino acid sequence.
Figures 4, 6B:
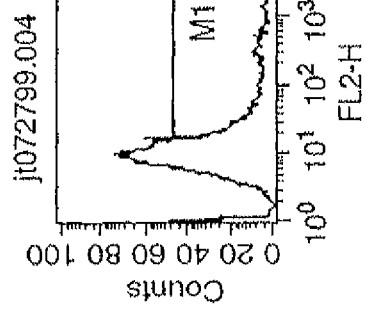
Figures 5, 6B:
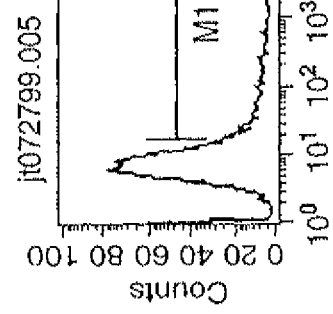
Figures 6, 6B:
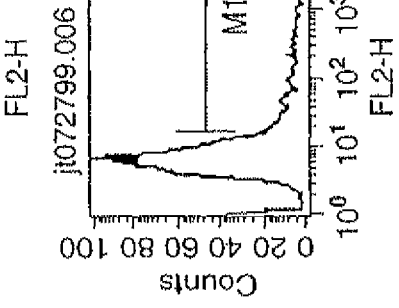
Figures 6, 6B, 7:
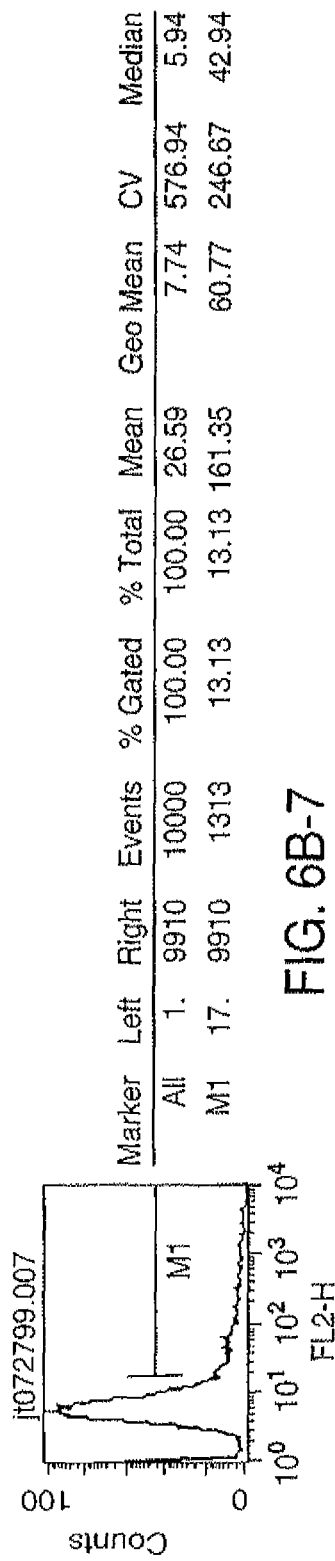
FIG. 7 shows immunoprecipitations with BAFF-R-Fc as described in methods in Example 4. Molecular weight standards in kDa are as labeled to the left of the figure. Lane (1) 12.5 ng flag-hTWEAK, (2) 12.5 ng flag-hBAFF, (3) immunoprecipitation of flag-hBAFF by 0.5 ml BAFF-R-Fc conditioned media, (4) immunoprecipitation of flag-hTWEAK by 0.5 ml BAFF-R-Fc conditioned media, (5) immunoprecipitation of no ligand by 0.5 ml BAFF-R-Fc conditioned media, (6) immunoprecipitation of flag-hBAFF by 0.5 ml conditioned media from untransfected 293EBNA, (7) immunoprecipitation of flag-hTWEAK by 0.5 ml conditioned media from untransfected 293EBNA.
Figures 6, 6B, 7, 8:
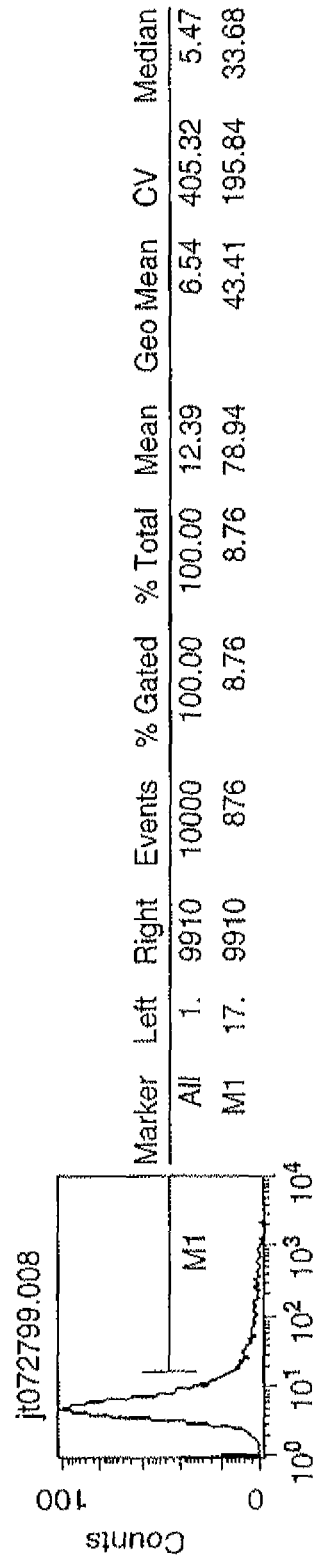
FIG. 8 shows a plot of the results of a splenocyte proliferation assay in which the counts per minute (CPM) incorporated into mouse splenocyte cells is plotted against the amount of human BAFF added (ug/ml).

FIG. 8 shows the results of the splenocyte Proliferation Assay. Shown are the counts per minute (CPM) incorporated into the mouse splenocyte cells vs. the amount of human BAFF reagent added. The level of anti-μ or fusion protein or control hIgG is held constant at 10 μg/ml. The solid squares represent the level of proliferation induced by BAFF alone. The solid circles represent the proliferation of the cells with BAFF and anti-μ. The curve with the open triangle represents the inhibition observed when BAFF-R: hIgG1BAFF is added with anti-μ plus BAFF-R:hIgG1. The open diamond represents the inhibition observed using control human Ig.

The addition of BAFF plus anti-μ results in the proliferation of mouse splenocytes in vitro. The level of $^3$H thymidine incorporated into the cells is significantly higher than the level obtained when either BAFF alone or anti-R alone is added to the splenocytes. The treatment of the splenocytes with BAFF alone results in $^3$H-thymidine incorporation only at very high concentrations. The addition of anti-μ alone results in no proliferation. When 10 μg/ml of control human Ig was added to the splenocytes with increasing amounts of BAFF and 10 μg/ml anti-μ, there was a modest decrease in the level of proliferation. In contrast, when 10 μg/ml of a human BAFF-R: hIgG1 fusion protein is added to the assay under the same conditions, the extent of proliferation is reduced to the level observed for the BAFF alone treatment. This indicates that the BAFF-R: hIgG1 fusion protein is capable of inhibiting the proliferation of splenocytes induced by BAFF and anti-μ.

Example 10

Blocking BAFF Binding to Raji Cells Using BAFF-R: hIgG1

In this example, pre-incubation of BAFF with BAFF-R: hIgG1 fusion protein resulting in the reduction of BAFF binding to the Raji B cell lymphoma line is described.

In this FACS assay, 200 ng/ml FLAG-tagged human BAFF was pre-incubated with either human BAFF-R: hIgG1 or human LTβR: hIgG1 at two fold dilutions ranging from 20 μg/ml to 39 ng/ml or no fusion protein for 30 min. on ice. The incubation took place in a FACS buffer containing PBS without $Ca^{2+}$ or $Mg^{2+}$ plus 10% FCS (JRH) and 0.05% sodium azide. After pre-incubation, the BAFF-fusion protein mixture was added to $5 \times 10^6$ Raji (ATCC) cells/ml. This incubation took place for 30 min. on ice and then the cells were washed with 2 ml of FACS buffer at 4° C. In order to detect the bound BAFF, 5 μg/ml of anti-FLAG antibody M2 (Sigma) was added to the cells and incubated for 30 min. on ice. The cells were again washed as above and then incubated with a 1:100 dilution of PE conjugated donkey anti-mouse Ig (Jackson Immuno Research) for 30 min. on ice. After the cells were washed again with FACS buffer, they were fixed with 1% paraformaldehyde and read by FACS® (Becton Dickinson and Co.)

Figures 6, 6B, 7, 8, 9:
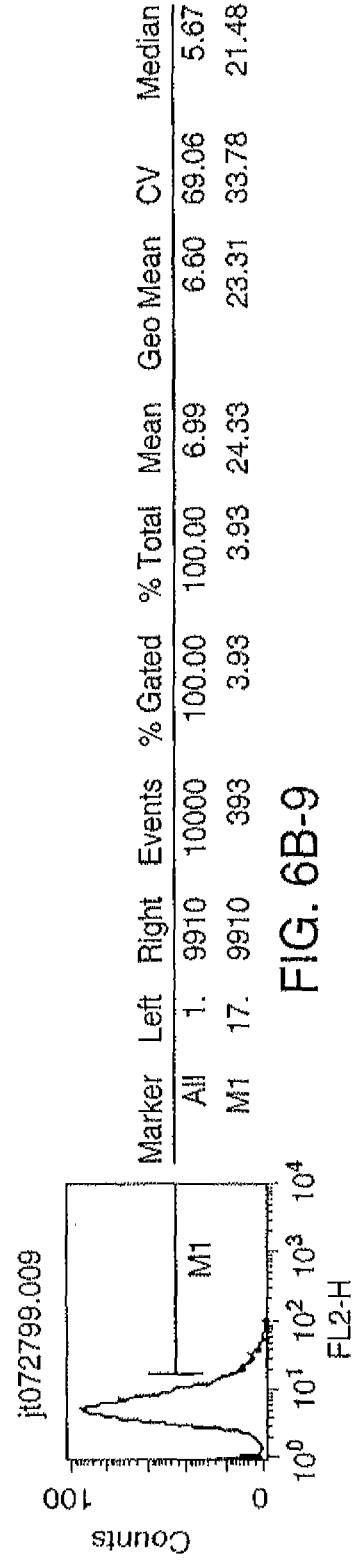
FIG. 9 shows a plot of the results of a BAFF blocking assay analyzing BAFF binding to Raji cells in which the MFI (mean fluorescence intensity) readings are plotted against the amount of R:hIgG1 (ng/ml).
Figure 7:
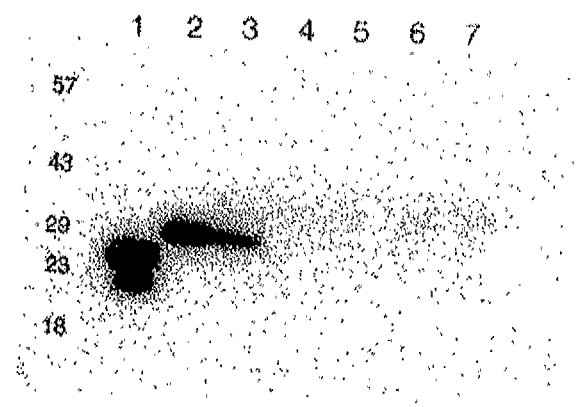
Figure 8:
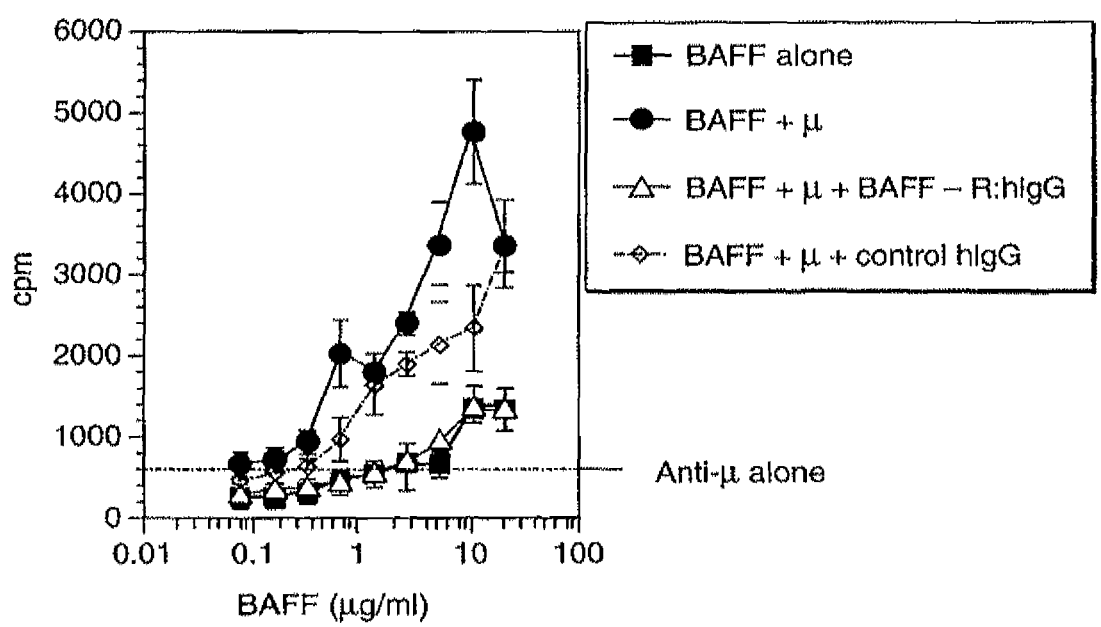
Figure 9:
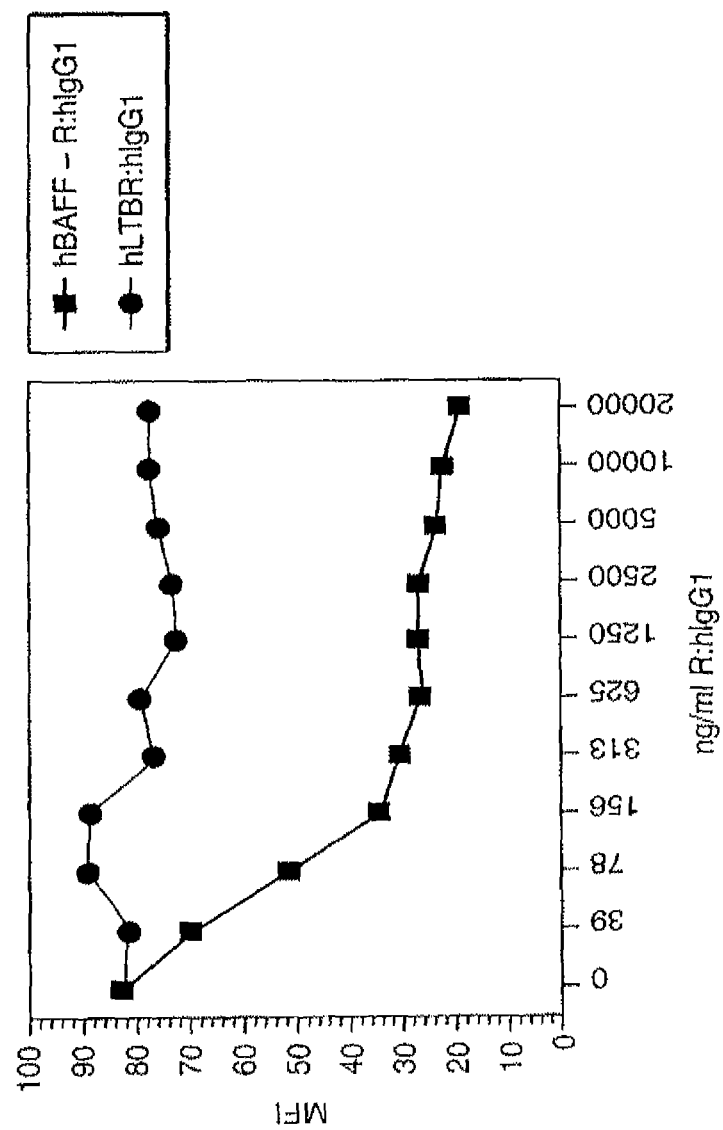

FIG. 9 shows the results of the BAFF blocking assay. Shown are the MFI (mean fluoresence intensity) readings resulting from a FACS® analysis examining BAFF binding to Raji cells. The solid squares represent the data when human BAFF-R: hIgG1 is pre-incubated with BAFF prior to binding to the cells. The circles show the curve resulting from addition of a non-specific fusion protein, human LTβR: hIgG1, to BAFF. The x-axis represents the amount of fusion protein added to 200 ng/ml BAFF prior to incubation with the cells.

When no fusion protein is pre-incubated with human BAFF, the mean fluorescence intensity (MFI), of the sample was 80. When human LTβR: hIgG1 is pre-incubated with BAFF, even at 20 μg/ml, the detection of BAFF binding to Raji cells is unchanged. When human BAFF-R: hIgG1 is pre-incubated with BAFF, however, there is a substantial decrease in the MFI, down to 20-25 even at 625 ng/ml fusion protein. The background MFI for this experiment is 7. Thus, BAFF-R: hIgG1 is very effective at blocking BAFF binding to Raji B cells.

Example 11

BAFF-R-IgG Attenuates Lupus-Like Autoimmune Disorders in Transgenic Mice

This example describes the effects of BAFF-R-Ig to reduce the peripheral B-cell pool and inhibit development of splenamegally and nephritis.

Five-month-old BAFF transgenic (Tg) mice (C57BL/6) and age-matched littermates were used in the experiment. BAFF Tg mice manifest lymphocytic disorders and an autoimmune phenotype similar to systemic lupus erythematosus (Mackay et al., 1999). This phenotype includes increased peripheral B cell populations including Transitional 1 (T1) and 2 (T2), mature (M), marginal zone (MZ) and $CD1^{high}/IgM^{high}$ B cells.

The mice received i.p. PBS, 400 mg of purified human IgG (Mg) (Sandoz, Basel, Switzerland) (3/group) or 400 μg of CHO-derived human BAFF-R-huIgG1 (hBCMA-Ig) fusion protein (2/group) on days 0, 4, 7, 11, 14, 18, 21, 25, 28, 32, 35 and were sacrificed at day 40.

At the time of sacrifice, spleen weight was measured and single cell suspensions were prepared after lysing red blood cells in a hypotonic buffer. Flow cytometry was performed using FITC-conjugated anti-CD21/CD35, PE-conjugated anti-IgD and anti-CD1, cychrome-conjugated anti-CD45R/B220 and biotin-conjugated anti-IgM. All mAbs were purchased from Pharmingen (San Diego, Calif.). Briefly, Fc receptors were blocked with 10 μg/ml Fc Block (Pharmingen) for 10 min on ice, followed by addition of biotin-conjugated mAbs for 30 min on ice, cells were washed 1×, followed by addition of FITC, is PE, Cychrome-conjugated Abs, strepavidin APC and 10 μg/ml Fc Block. Cells were incubated for 30 min on ice, washed 1× and suspended in 0.5% paraformaldehyde. Cell fluorescence data were acquired on a FACS-Calibur (flow cytometer (Becton Dickinson, San Jose, Calif.) and analyzed using CELLQuest (software (Becton Dickinson).

The presence of proteins in mouse urine was measured using Multistix 10 SG reagent strips for urinalysis (Bayer Corp., Diagnostics Division).

Results are shown in Tables 11A and 11B below:

TABLE 11A

3 Month Splenocyte Analysis

| | Total Cells per Spleen (×10$^6$) | | | |
|---|---|---|---|---|
| | T1 | T2 | MZ | Mature |
| BAFF Tg Mice | | | | |
| 816E23 | 9.4 | 18 | 9 | 91 |
| 816E33 | 14 | 30 | 19 | 170 |
| 816E99 | 14 | 24 | 19 | 150 |
| Mean | 13 +/2.6 | 24 +/− 6 | 16 +/5.7 | 140 +/− 41 |
| Littermate Controls | | | | |
| 816E2 | 5.3 | 5.8 | 3.1 | 73 |
| 816E4 | 2.4 | 3.7 | 1.9 | 44 |
| Mean | 3.9 +/− 2 | 4.8 +/− 1.5 | 2.4 +/− 1 | 59 +/− 20 |

The spleens of the 3 month old Baff Tg mice (n=3) and age-matched littermates (n=2) were isolated and subjected to FACS analyses as described in the Materials and Methods. The T1, T2, M and MZ cells were defined by the expression of the following surface markers (hi: high., lo: low., int: intermediate):

T1:IgD$^-$, IgM$^{high}$, CD21$^{lo}$
MZ:IgD$^-$, IgM$^{hi}$, CD21
T2:IgD$^+$, IgM$^{hi}$, CD21$^{hi}$
M:IgD$^+$, IgM$^{lo}$, CD21$^{int}$

TABLE 11B

10 Month Splenocyte Analysis

| | Total Cells per Spleen (×10$^6$) | | | |
|---|---|---|---|---|
| | T1 | T2 | MZ | Mature |
| BAFF Tg Mice | | | | |
| 802-39 | 13 | 100 | 34 | 630 |
| 823-3-11 | 7.5 | 43 | 6.6 | 200 |
| 823-3-13 | 3.1 | 50 | 15 | 180 |
| Mean | 7.9 +/− 4.9 | 64 +/− 30 | 19 +/− 10 | 340 +/− 250 |
| Littermate | | | | |

TABLE 11B-continued

10 Month Splenocyte Analysis

| | Total Cells per Spleen (×10$^6$) | | | |
|---|---|---|---|---|
| | T1 | T2 | MZ | Mature |
| Controls | | | | |
| 823-3-22 | 0.7 | 6.5 | 1.4 | 56 |
| 802-64 | 0.28 | 5.4 | 1.3 | 38 |
| 823-14-13 | 0.45 | 3.4 | 0.16 | 38 |
| Mean | 0.48 +/− 0.21 | 5.1 +/− 1.5 | 0.95 +/− 0.65 | 44 +/− 10 |

10 month old Baff Tg mice (n=3) and age-matched littermates (n=3) were subjected to FACS analyses as described in Table 1.

Figure 10C:
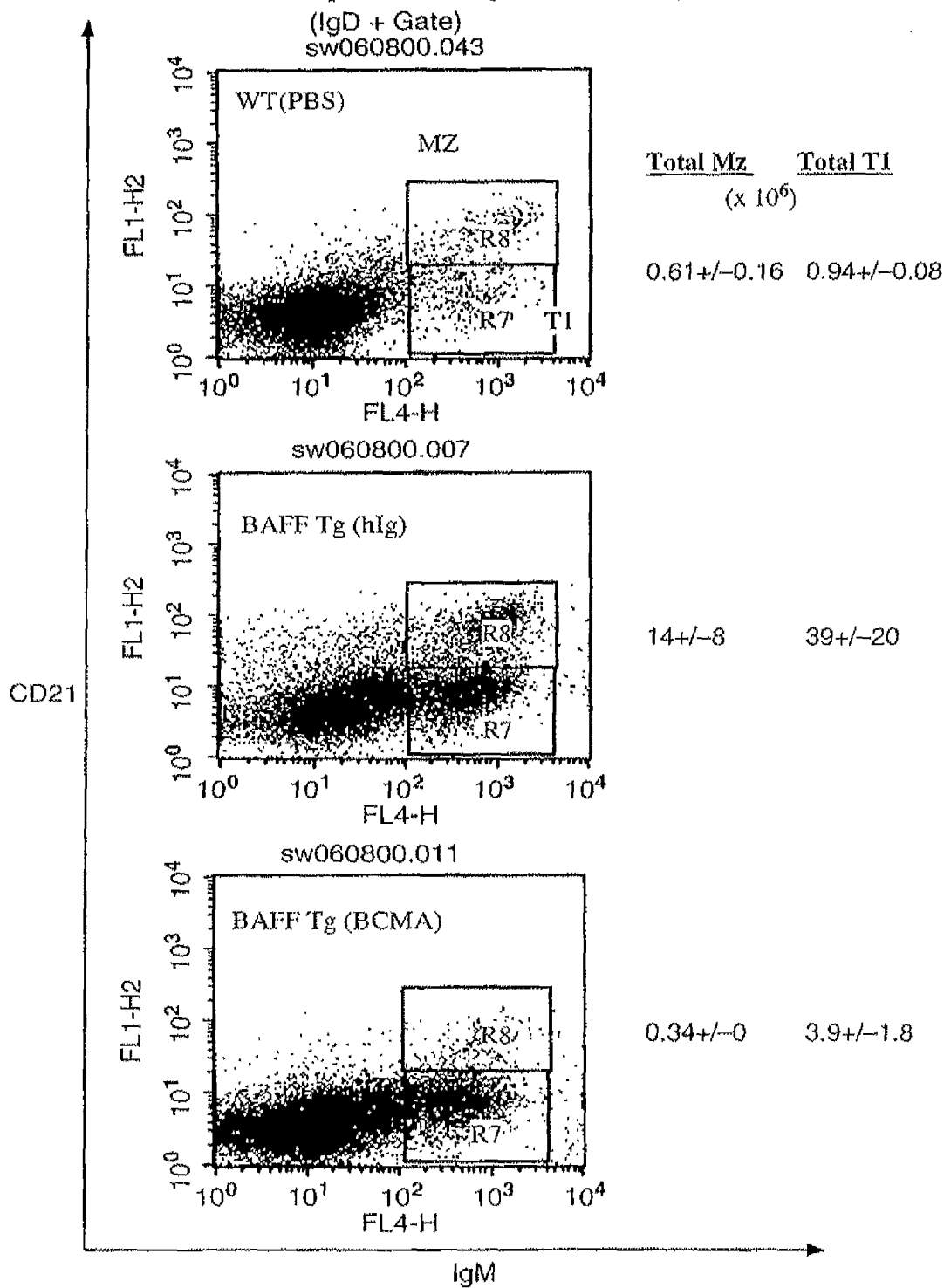
FIG. 10(c) shows plots of the expression of CD21 vs. IgM in FACS analysis by gating on IgD negative populations for Baff Tg mice that received h-Ig (middle panel) or hBCMA-Ig (lower panel) and for wildtype littermate controls that received PBS injections (upper panel), as described in Example 11.

After administration of h BAFF-R-Ig to Baff Tg mice the T1, T2, M, MZ populations and the CD1$^{high}$/IgM$^{high}$ B cells in the spleen were reduced significantly as compared to the PBS and hIg treated Baff Tg mice, the total numbers of T1, T2, M, MZ and CD1$^{high}$/IgM$^{high}$ B cells were reduced to the level similar or lower than that of the control littermates treated with PBS (FIG. 10a, 10b, 10c).

Figure 11:
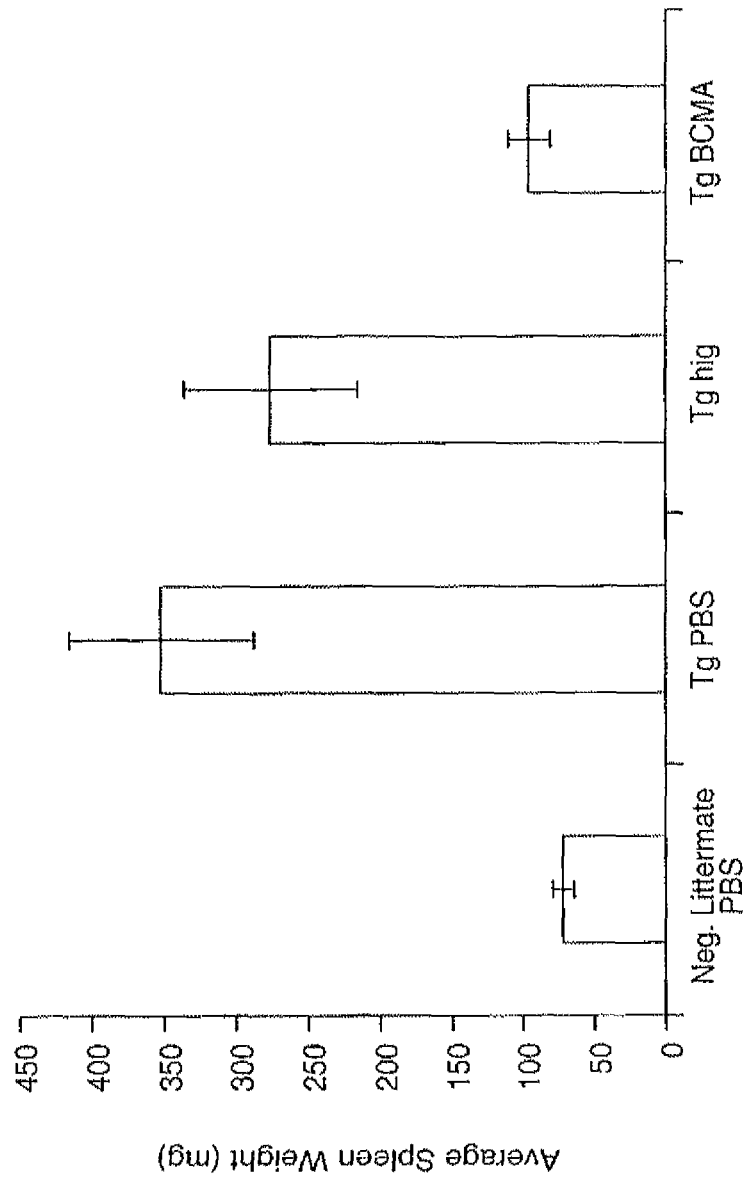
FIG. 11 shows spleen weights for all groups of Baff Tg mice (given as weight in mg+/− standard deviation).
Figure 12:
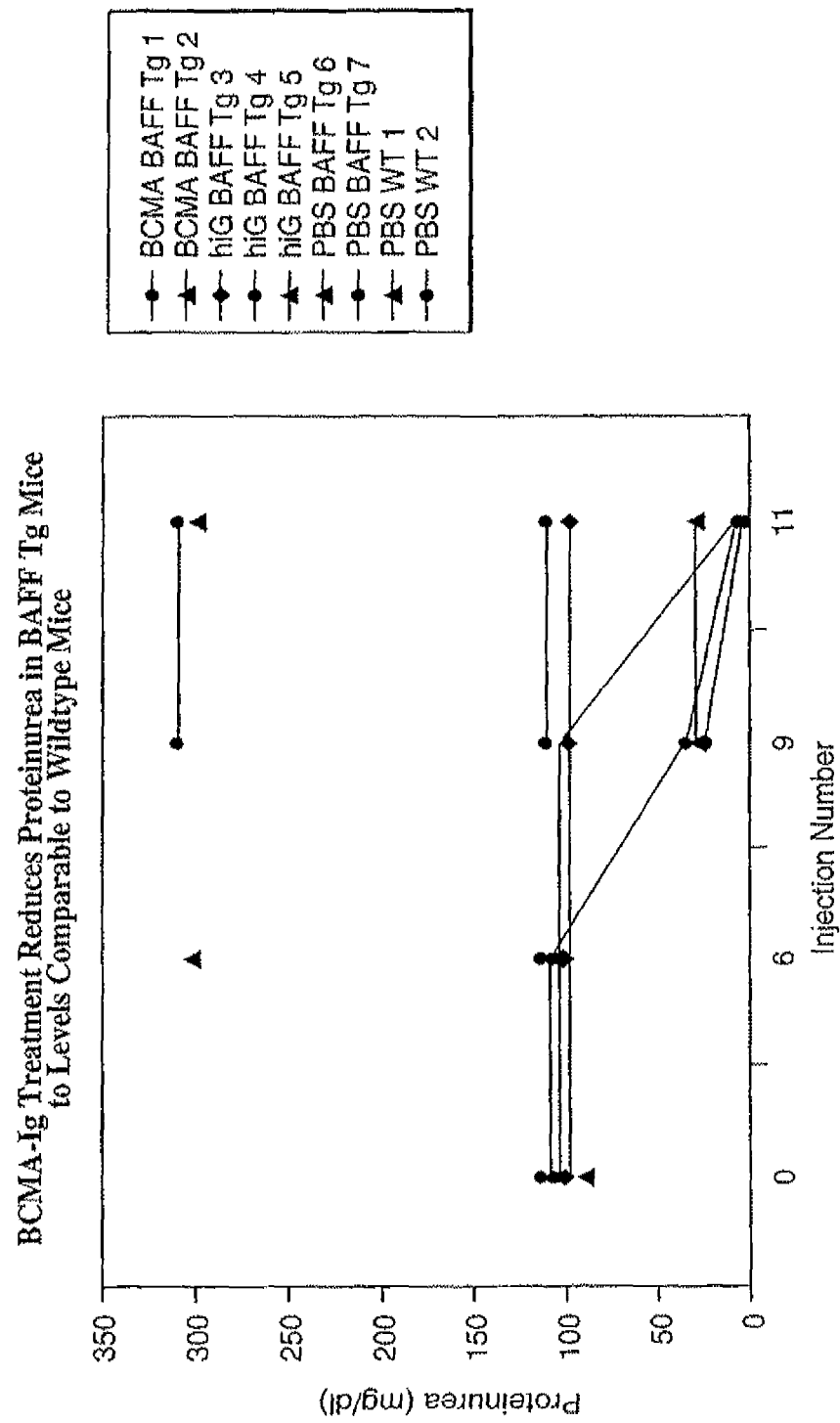
FIG. 12 shows a plot of proteinurea (mgldL) vs. injection number for Baff Tg mice treated with PBS, hIg, hBCMA-Ig and for littermate controls.

BAFF-R-Ig treatment of Baff Tg mice resulted in an attenuation of Baff-mediated autoimmune disease as evidenced by the observation that BAFF-R-treated mice had spleens of normal size while control-treated Baff Tg mice exhibited splenamegaly (FIG. 11). In addition, the development of proteinuria, an indicator of renal dysfunction, was inhibited in BAFF-R-Ig treated mice, whereas control-treated Baff Tg mice developed nephritis as determined by rising proteinuria levels (FIG. 12).

Mice transgenic for Baff have vastly increased numbers of peripheral B cells, and our further analysis revealed predominantly increased T1, T2, MZ B cell subpopulations in these mice. The transitional stage of B cell development (T1 and T2) is the checkpoint at which autoreactive B cells are presumably eliminated. CD1$^{hi}$/IgM$^{high}$ B cells, which tend to reside in the marginal zone, were also highly increased in Baff Tg mice. This latter population of B cells was shown to be the major source of autoantibody production in NZB/NZW lupus mice. Treatment of Baff Tg mice with BAFF-R-Ig results in a reduction of the T1, T2, MZ and CD 1$^{hi}$ B cell populations to levels similar to or lower than those found in wildtype littermate controls.

BAFF-R-Ig functioned to reduce the peripheral B cell pool and inhibit development of splenamegally and nephritis. Therefore, in addition to its usefulness in systemic lupus erythematosus lupus nephritis, the action of BAFF-R-Ig is also useful as in B cell-mediated diseases that are autoimmune in nature such as myasthenia gravis, autoimmune hemolytic anemia, idiopathic thrombocytopenia purpura, anti-phospholipid syndrome, Chaga's disease, Grave's disease, Wegener's Granulomatosis, Poly-arteritis Nodosa and Rapidly Progressive Glomerulonephritis. This therapeutic agent also has application in plasma cell disorders such as multiple myeloma, Waldenstrom" macroglobulinemia, Heavey-chain disease, Primary or immunocyte-associated amyloidosis, and Monoclonal gammopathy of undetermine significance (MGUS). Oncology targets include B cell carcinomas, leukemias, and lymphomas.

Example 12

Mean Arterial Pressure in BAFF Transgenic Mice

This experiment describes the measurement of blood pressure in BAFF transgenic mice. Observations made during phenotype evaluation of BAFF transgenic mice indicated the potential for hypertension in the mice.

Baff Tg mice as described above were anesthetized with ketamine. The left carotid artery was exposed via an incision in the neck. A catheter was inserted into the carotid artery for measurement of blood pressure and heart rate. The catheter was connected to a pressure transducer and blood pressure was measured using a Gould data acquisition system (Po-Ne-Mah Data Acquisition system and Gould polygraph). From the pulsatile pressure waveform, systolic pressure, diastolic pressure, mean pressure and heart rate were derived. Two groups of mice were used: BAFF transgenics (n=8) and Wild-Type Controls (n=9).

Figure 13:
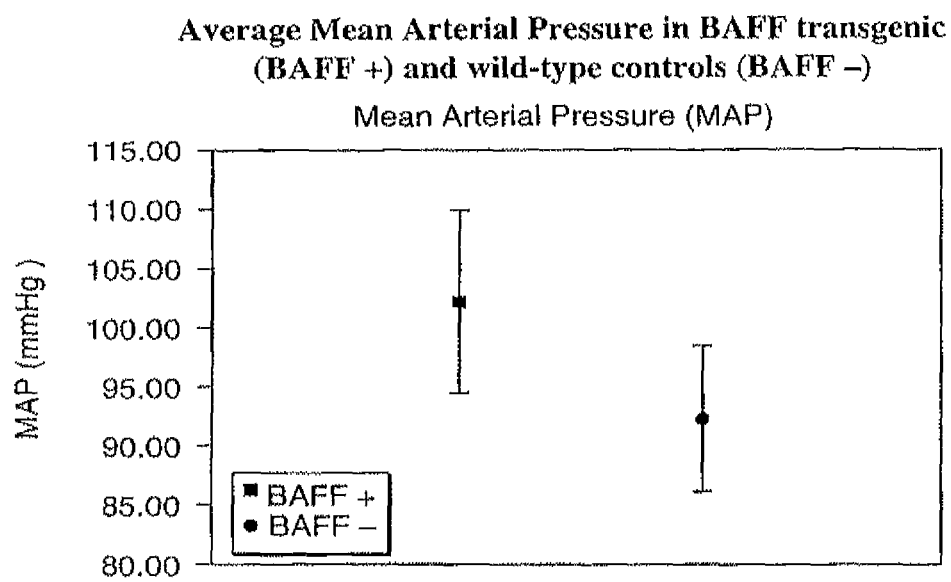
FIG. 13 shows a plot of the average mean arterial pressure (mmHg) in Baff Tg mice and wildtype controls.

FIG. 13 displays the average mean arterial pressure (MAP, in mmHg) for the two groups. As shown, the BAFF transgenic mice had an average MAP of 102±8 mmHg. The control mice had an average MAP of 92±6 mmHg. Thus, the BAFF mice demonstrate a 10 mmHg increase in MAP over controls, although this did not achieve statistical significance (ANOVA).

Figure 14:
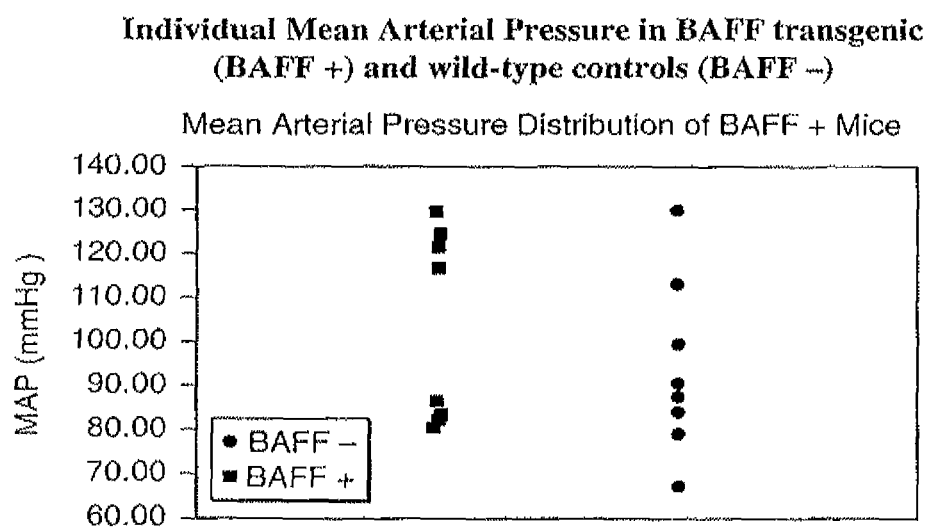
FIG. 14 shows a plot of the individual mean arterial pressure (mmHg) for Baff Tg mice and wildtype controls.

More detailed analysis of the data are shown in FIG. 14. In this figure, the results from individual animals are displayed. In the wild-type controls (BAFF−), the distribution of the data follow a typical, binomial distribution. In contrast, the pressures in the BAFF transgenic mice (BAFF+) appear as if they distribute into two groups, with one group in the 120-130 mmHg range and one group in the 80-90 mmHg range.

As a population, the BAFF transgenic mice have a tendency towards hypertension, as compared to negative control mice. Analysis of individual levels of arterial pressure indicate the BAFF transgenic mice are distributed into two subpopulations, one with high blood pressure and one with normal blood pressure. Accordingly, administering a soluble BAFF-R, fusion protein or antibody homolog can ameliorate the effects of hypertension.

Example 13

BAFF-R-Ig Treatment of SNF$_1$ Mice with Established Disease Slows Progression to Severe Nephritis Female lupus-prone (SWR×NZB)F1 (SNF$_1$) mice, aged 21 weeks and exhibiting moderate nephritis (30-100 mg/dl proteinuria), received 200 µg of fusion protein human BAFF-R-huIgG1 (hBCMA-Ig), human IgG (HuIgG) (Sandoz), or 200 µl of PBS i.p. weekly for 8 weeks. The urine of each mouse was monitored weekly for proteinuria using Albustix (Bayer Corp., Terrytown, N.Y.). Proteinuria over 100 mg/dl was scored as severe nephritis. BAFF-R-Ig was produced from transiently transfected EBNA 293 cells. Conditioned media from 293 cells over-expressing hBCMA-Ig was loaded onto a protein A column. Protein was eluted using 25 mM phosphate 100 mM NaCl pH 2.8 following by neutralization with 1/20 volume of 0.5 M NaPO4 pH 8.6. Selected fractions based in OD280 were subjected to reducing and non-reducing SDS-PAGE gels and Western blots to identify the purified protein.

Figure 15:
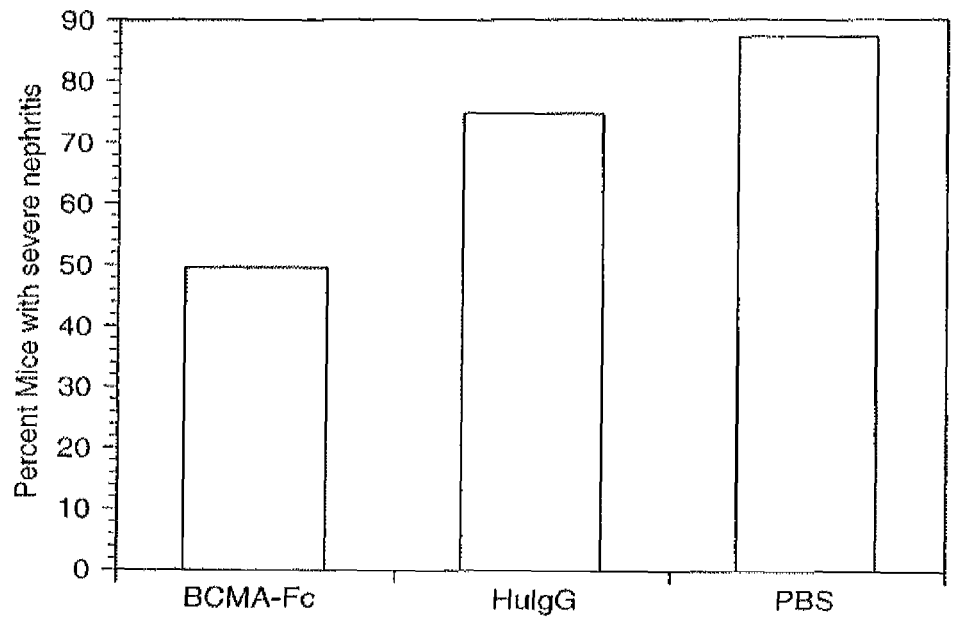
FIG. 15 shows a bar graph of the percentage of SNF1 mice that display severe nephritis after treatment with BAFF-R-Ig (BCMA-Ig), HuIgG or PBS.

Three weeks after treatment was terminated 50% of mice treated with BAFF-R-Ig exhibited severe nephritis, compared to 75% and 87.5% of mice that received HuIgG and PBS, respectively (see FIG. 15). These data demonstrate that the soluble BAFF receptor, BCMA-Ig, can function to block B cell-mediated autoimmune disease, such as lupus nephritis, resulting in a marked delay in disease progression.

Example 14

BAFF-R-Ig Treatment of Normal Mice Results in a Reduction in the Number of Splenic Dendritic Cells (DC) and an Atypical Splenic Localization Seven-week-old female BALB/c mice (3/group) were given i.p. either 20 µg or 50 µg human BAFF-R-IgG1 (hBCMA-Ig), 50 µg human IgG (HuIgG) or 100 µl PBS 1×/week for 4 weeks. The hBCMA-Ig fusion protein was purified from culture supernatants of a stably transfected CHO cell line. Spleens were obtained 8 days after the last injection and digested with collagenase (Sigma cat. #C-5138) for 1 hr. at 37° C. A single cell suspension was prepared, RBCs were lysed in a hypotonic buffer, and the cells were washed 3× in PBS. Splenocytes were prepared for flow cytometric analysis by staining cells with anti-CD11c-biotin followed by streptavidin-APC, anti-CD8a-cychrome, and anti-CD4-FITC to assess DC populations.

In a separate experiment female BALB/c (N=3) mice were given i.p. 100 µg hBCMA-Ig 1×/week for 4 weeks after which spleens were snap frozen in OCT using 2-methyl butane chilled on $CO_2$. Cryosections were cut and fixed in acetone. Sections were incubated with anti-CD11c-biotin followed by streptavidin-AP and substrate BCIP (Pierce) to visualize DCs, mAb MOMA-1 followed by anti-rat IgG-HRP (Jackson ImmunoResearch) and substrate 3,3' diaminobenzidine (Sigma, St. Louis Mo., Cat. #D-1293) to visualize metallophilic macrophages, and anti-CD35-biotin followed by streptavidin AP and substrate (Alkaline Phosphatase Substrate Kit I, Vector cat#SK-5100) to visualize follicular dendritic cells (FDC).

Figure 16:
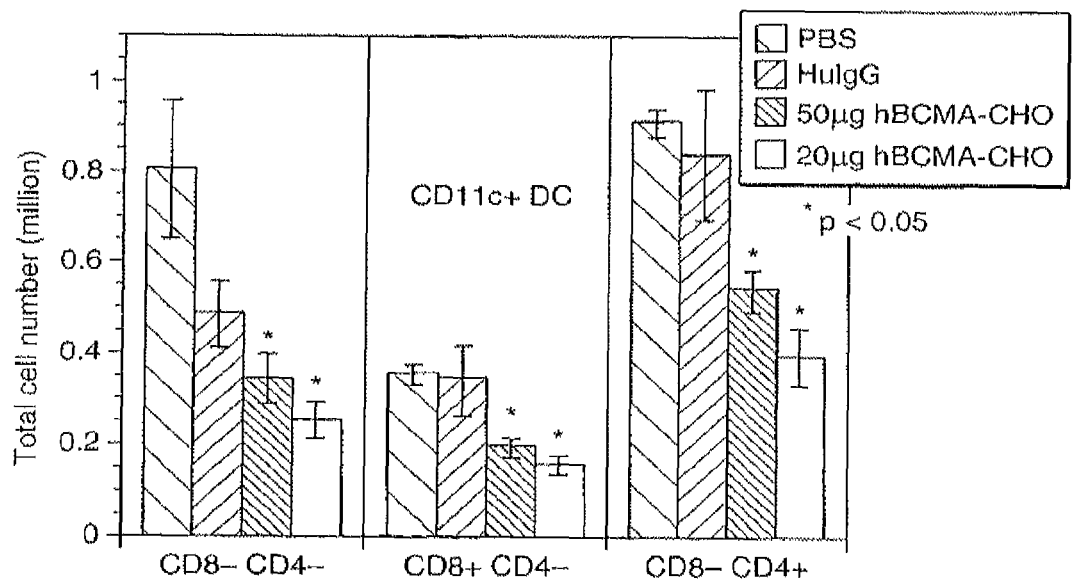
FIG. 16 shows a graph of the total CD11c+DC cell number (in millions) for mice treated in vivo with 20 ug BCMA-Ig, 50 ug BCMA-Ig, HuIgG or PBS. CD11c+DC cell populations examined were: (1) CD8a−CD4−, (2) CD8a+CD4−, and (3) CD8a−CD4+.

Mice treated in vivo with either 20 µg or 50 µg of BCMA-Ig 1×/week for 4 weeks exhibited a significant decline (p<0.05 by Student's t test) in splenic CD11c+DCs as compared to HuIgG and PBS-treated controls. This decline was seen for all CD11c+DC populations examined: CD8a−CD4−, CD8a+CD4−, and CD8a−CD4+ (FIG. 16, Table 14A).

TABLE 14A

BAFF-R-Ig treatment results in a reduction in the number of splenic DCs.

|  | PBS | HuIgG | 20 µg BCMA-Ig | 50 µg BCMA-Ig |
|---|---|---|---|---|
|  | Mean number of CD11+ DCs (×10$^6$) ± SD | | | |
| CD8a−CD4− | 0.81 ± 0.15 | 0.49 ± 0.07 | 0.26 ± 0.04 | 0.35 ± 0.05 |
| CD8a+CD4− | 0.36 ± 0.02 | 0.35 ± 0.07 | 0.16 ± 0.02 | 0.2 ± 0.02 |
| CD8a−CD4+ | 0.92 ± 0.02 | 0.84 ± 0.15 | 0.4 ± 0.06 | 0.55 ± 0.04 |

This decline in splenic DCs, which are critical antigen presenting cells, may impact B cell activation, maturation and humoral immunity.

Frozen spleen sections were obtained from mice as described in Materials and Methods. BCMA-Ig-treated mice exhibited an atypical DC homing pattern when stained with anti-CD11c. DCs normally localize within the T cell area of the white pulp and within the marginal zone, with a concentration at the marginal zone bridging channels. However, DCs from BCMA-Ig-treated mice were found surrounding the perimeter of the marginal zone and few appeared to be able to migrate further within the white pulp (data not shown). Therefore, blocking BAFF/BAFF-R interaction with soluble BAFF receptor appears to interfere with the homing pattern of DCs which may affect their ability to function as antigen presenting cells, thereby impacting B cell activation, maturation and humoral immunity. Furthermore, the spleens of BCMA-Ig-treated mice lacked CD35+ FDCs as determined by immunohistochemistry (data not shown). Since FDCs function to present antigen to B cells within germinal centers (GC), lack of such cells could have a detrimental effect on GC structure and B cell affinity maturation.

It will be apparent to those skilled in the art that various modifications and variations to can be made in the polypeptides, compositions and methods of the invention without departing from the spirit or scope of the invention. Thus, it is intended that the present invention cover the modifications and variations of this invention provided that they come within the scope of the appended claims and their equivalents.

SEQUENCE LISTING

<160> NUMBER OF SEQ ID NOS: 8

<210> SEQ ID NO 1
<211> LENGTH: 184
<212> TYPE: PRT
<213> ORGANISM: homo sapien

<400> SEQUENCE: 1

Met Leu Gln Met Ala Gly Gln Cys Ser Gln Asn Glu Tyr Phe Asp Ser
 1               5                  10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 552
<212> TYPE: DNA
<213> ORGANISM: homo sapien

<400> SEQUENCE: 2
atgttgcaga tggctgggca gtgctcccaa aatgaatatt ttgacagttt gttgcatgct      60
tgcataccct tgtcaacttc gatgttcttc aatactcctc ctctaacatg tcaggttatt     120
gtaatgcaag tgtgaccaat tcagtgaaag gaacgaatgc gattctctgg acctgtttgg     180
gactgagctt aataatttct ttggcagttt tcgtgctaat gttttgcta aggaagataa      240 gctctgaacc attaaaggac gagtttaaaa acacaggatc aggtctcctg ggcatggcta     300
acattgacct ggaaaagagc aggactggtg atgaaattat tctccgagag gcctcgagta     360
cacggtggaa gaatgcacct gtgaagactg catcaagagc aaaccgaagg tcgactctga     420
ccattgcttt ccactcccag ctatggagga aggcgcaacc attctgtcac cacgaaaacg     480
aatgactatt gcaagagcct gccagctgct ttgagtgcta cggagataga gaatcaatt      540 tctgctaggt aa                                                         552

<210> SEQ ID NO 3
<211> LENGTH: 207
<212> TYPE: PRT
<213> ORGANISM: homo sapien

-continued

<400> SEQUENCE: 3

```
Met Asp Thr Leu Leu Leu Trp Val Leu Leu Trp Val Pro Gly Ser
 1               5                  10                  15

Thr Gly Met Leu Gln Met Ala Gly Gln Cys Ser Gln Asn Glu Tyr Phe
             20                  25                  30

Asp Ser Leu Asp Val Thr Met Leu Gln Met Ala Gly Gln Cys Ser Gln
             35                  40                  45

Asn Glu Tyr Phe Asp Ser Leu Leu His Ala Cys Ile Pro Cys Gln Leu
         50                  55                  60

Arg Cys Ser Ser Asn Thr Pro Pro Leu Thr Cys Leu His Ala Cys Ile
 65                  70                  75                  80

Pro Cys Gln Leu Arg Cys Ser Ser Asn Thr Pro Pro Leu Thr Cys Gln
                 85                  90                  95

Arg Tyr Cys Asn Ala Ser Val Thr Asn Ser Val Lys Gly Gln Arg Tyr
                100                 105                 110

Cys Asn Ala Ser Val Thr Asn Ser Val Lys Gly Val Asp Lys Thr His
                115                 120                 125

Thr Cys Pro Pro Cys Pro Ala Pro Glu Leu Leu Gly Gly Pro Ser Val
        130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
                180                 185                 190

Thr Lys Pro Arg Glu Glu Gln Tyr Asn Ser Tyr Val Val Ser Val
            195                 200                 205
```

<210> SEQ ID NO 4
<211> LENGTH: 540
<212> TYPE: DNA
<213> ORGANISM: homo sapien

<400> SEQUENCE: 4

```
atggagacag acacactcct gttatgggtg ctgctgctct gggttccagg ttccactggt    60
gacgtcacga tgttgcagat ggctgggcag tgctcccaaa atgaatattt tgacagtttg   120
ttgcatgctt gcataccttg tcaacttcga tgttcttcta atactcctcc tctaacatgt   180
cagcgttatt gtaatgcaag tgtgaccaat tcagtgaaag gagtcgacaa aactcacaca   240
tgcccaccgt gcccagcacc tgaactcctg ggggaccgt cagtcttcct cttccccca    300
aaacccaagg acaccctcat gatctcccgg acccctgagg tcacatgcgt ggtggtggac   360
gtgagccacg aagaccctga ggtcaagttc aactggtacg tggacggcgt ggaggtgcat   420
aatgccaaga caaagccgcg ggaggagcag tacaacagca cgtaccgtgt ggtcagcgtc   480
ctcaccgtcc tgcaccagga ctggctgaat ggcaaggagt acaagtgcaa ggtctccaac   540
```

<210> SEQ ID NO 5
<211> LENGTH: 140
<212> TYPE: PRT
<213> ORGANISM: homo sapien

<400> SEQUENCE: 5

```
Leu Thr Val Leu His Gln Asp Trp Leu Asn Gly Lys Glu Tyr Lys Cys
 1               5                  10                  15
```

```
Lys Val Ser Asn Lys Ala Leu Pro Ala Pro Ile Glu Lys Thr Ile Ser
            20                  25                  30

Lys Ala Lys Gly Gln Pro Arg Glu Pro Gln Val Tyr Thr Leu Pro Pro
        35                  40                  45

Ser Arg Asp Glu Leu Thr Lys Asn Gln Val Ser Leu Thr Cys Leu Val
    50                  55                  60

Lys Gly Phe Tyr Pro Ser Asp Ile Ala Val Glu Trp Glu Ser Asn Gly
65                  70                  75                  80

Gln Pro Glu Asn Asn Tyr Lys Thr Thr Pro Pro Val Leu Asp Ser Asp
                85                  90                  95

Gly Ser Phe Phe Lys Lys Leu Thr Val Asp Lys Ser Arg Trp Gln Gln
            100                 105                 110

Gly Asn Val Phe Ser Cys Ser Val Met His Glu Ala Leu His Asn His
        115                 120                 125

Tyr Thr Gln Lys Ser Leu Ser Leu Ser Pro Gly Lys
    130                 135                 140

<210> SEQ ID NO 6
<211> LENGTH: 369
<212> TYPE: DNA
<213> ORGANISM: homo sapien

<400> SEQUENCE: 6
aaagccctcc cagcccccat cgagaaaacc atctccaaag ccaaagggca gccccgagaa    60
ccacaggtgt acaccctgcc cccatcccgg gatgagctga ccaagaacca ggtcagcctg   120
acctgcctgg tcaaaggctt ctatcccagc gacatcgccg tggagtggga gagcaatggg   180
cagccggaga acaactacaa gaccacgcct cccgtgttgg actccgacgg ctccttcttc   240
ctctacagca agctcaccgt ggacaagagc aggtggcagc aggggaacgt cttctcatgc   300
tccgtgatgc atgaggctct gcacaaccac tacacgcaga agagcctctc cctgtctccc   360
gggaaatga                                                            369

<210> SEQ ID NO 7
<211> LENGTH: 184
<212> TYPE: PRT
<213> ORGANISM: homo sapien

<400> SEQUENCE: 7

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
```

```
            130                 135                 140
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 8
<211> LENGTH: 995
<212> TYPE: DNA
<213> ORGANISM: homo sapien

<400> SEQUENCE: 8
aagactcaaa cttagaaact tgaattagat gtggtattca aatccttacg tgccgcgaag    60
acacagacag cccccgtaag aacccacgaa gcaggcgaag ttcattgttc tcaacattct   120
agctgctctt gctgcatttg ctctggaatt cttgtagaga tattacttgt ccttccaggc   180
tgttctttct gtagctccct tgtttctctt ttgtgatcat gttgcagatg gctgggcagt   240
gctcccaaaa tgaatatttt gacagtttgt tgcatgcttg cataccttgt caacttcgat   300
gttcttctaa tactcctcct ctaacatgtc agcgttattg taatgcaagt gtgaccaatt   360
cagtgaaagg aacgaatgcg attctctgga cctgtttggg actgagctta ataatttctt   420
tggcagtttt cgtgctaatg tttttgctaa ggaagataag ctctgaacca ttaaaggacg   480
agtttaaaaa cacaggatca ggtctcctgg gcatggctaa cattgacctg gaaaagagca   540
ggactggtga tgaaattatt cttccgagag gcctcgagta cacggtggaa gaatgcacct   600
gtgaagactg catcaagagc aaaccgaagg tcgactctga ccattgcttt ccactcccag   660
ctatggagga aggcgcaacc attcttgtca ccacgaaaac gaatgactat tgcaagagcc   720
tgccagctgc tttgagtgct acggagatag agaaatcaat ttctgctagg taattaacca   780
tttcgactcg agcagtgcca ctttaaaaat cttttgtcag aatagatgat gtgtcagatc   840
tctttaggat gactgtattt ttcagttgcc gatacagctt tttgtcctct aactgtggaa   900
actctttatg ttagatatat ttctctaggt tactgttggg agcttaatgg tagaaacttc   960
cttggtttca tgattaaagt cttttttttt cctga                              995
```

What is claimed is:

1. A method of screening for a compound that inhibits the interaction between BAFF (B-cell activating factor of the TNF family) and BCMA (B Cell Maturation Antigen), wherein the method comprises performing an ELISA (enzyme-linked immunosorbent assay) to test a compound for the ability to inhibit soluble BAFF from binding to a BCMA-Ig fusion protein comprising amino acid residues 1 to 51 of SEQ ID NO:1, and wherein the BCMA-Ig fusion protein does not comprise the transmembrane domain of BCMA (amino acids 53 to 81 of SEQ ID NO:1).

2. The method of claim 1, wherein prior to testing the compound for the ability to inhibit soluble BAFF from binding to a BCMA-Ig fusion protein, the compound is tested for the ability to bind to a BCMA-Ig fusion protein.

* * * * *